(12) United States Patent
Acosta et al.

(10) Patent No.: US 7,024,246 B2
(45) Date of Patent: Apr. 4, 2006

(54) AUTOMATIC WAVEFORM OUTPUT ADJUSTMENT FOR AN IMPLANTABLE MEDICAL DEVICE

(75) Inventors: Carlos C. Acosta, Tempe, AZ (US);
Leroy L. Perz, Buffalo, MN (US);
Carleen J. Juran, Shoreview, MN (US); Kevin L. Bright, Maple Grove, MN (US); Richard E. Hester, Phoenix, AZ (US)

(73) Assignee: Medtronic, Inc, Minneapolis, MN (US)

( * ) Notice: Subject to any disclaimer, the term of this patent is extended or adjusted under 35 U.S.C. 154(b) by 623 days.

(21) Appl. No.: 10/133,961

(22) Filed: Apr. 26, 2002

(65) Prior Publication Data

US 2003/0204226 A1    Oct. 30, 2003

(51) Int. Cl.
*A61N 1/36* (2006.01)
(52) U.S. Cl. .......................................... 607/46
(58) Field of Classification Search .......... 607/7, 607/8, 9, 11, 46, 62–64, 48, 52
See application file for complete search history.

(56) References Cited

U.S. PATENT DOCUMENTS

| | | | |
|---|---|---|---|
| 4,379,462 A | 4/1983 | Borkan et al. | |
| 4,459,989 A | 7/1984 | Borkan | |
| 4,690,145 A | 9/1987 | King-Smith et al. | |
| 5,501,703 A | 3/1996 | Holsheimer et al. | |
| 5,591,211 A | 1/1997 | Meltzer | |
| 5,643,330 A | 7/1997 | Holsheimer et al. | |
| 5,713,922 A | 2/1998 | King | |
| 5,895,416 A | 4/1999 | Barreras, Sr. et al. | |
| 5,925,070 A | 7/1999 | King et al. | |
| 5,948,004 A | 9/1999 | Weijand et al. | |
| 6,083,252 A | 7/2000 | King et al. | |
| 6,241,751 B1 | 6/2001 | Morgan et al. | |
| 6,304,781 B1 * | 10/2001 | Busch et al. .................. 607/8 |

FOREIGN PATENT DOCUMENTS

DE    10127810 A1    4/2002

* cited by examiner

*Primary Examiner*—George R. Evanisko
(74) *Attorney, Agent, or Firm*—Banner & Witcoff, Ltd.

(57) ABSTRACT

Apparatus and method assure the electrical characteristics of a stimulation waveform to an electrode of an Implantable Neuro Stimulator. The embodiment comprises a regulator, a measurement module, a generator, and a processor. The generator provides an input signal to the regulator. The regulator consequently regulates the input signal in order to form a pulse that is applied to the electrode. The processor instructs the measurement module to perform an electrical measurement that is indicative of an amplitude of the pulse. If the electrical measurement is sufficiently different from a desired value, the processor instructs the generator to be reconfigured in order that the amplitude of the pulse is within an acceptable value. A redundant capacitor pair may be inserted in a capacitor arrangement in order to compensate for a reduced battery voltage, or a detected faulty component such as a capacitor or a regulator may be replaced with a redundant component.

25 Claims, 26 Drawing Sheets

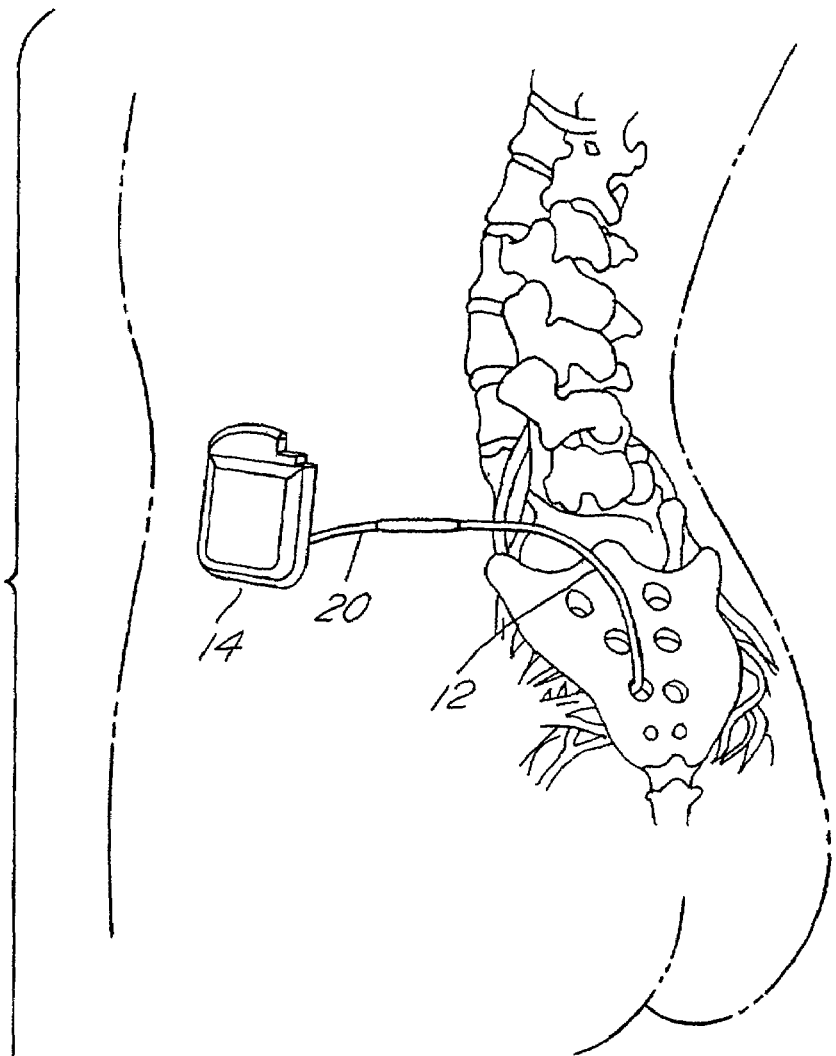
FIG.1
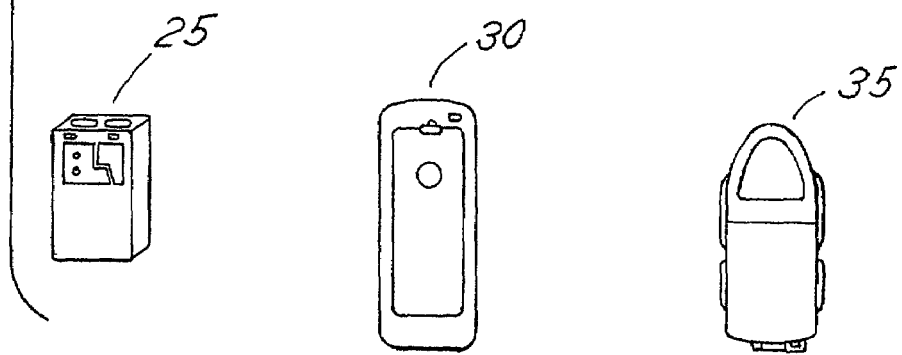

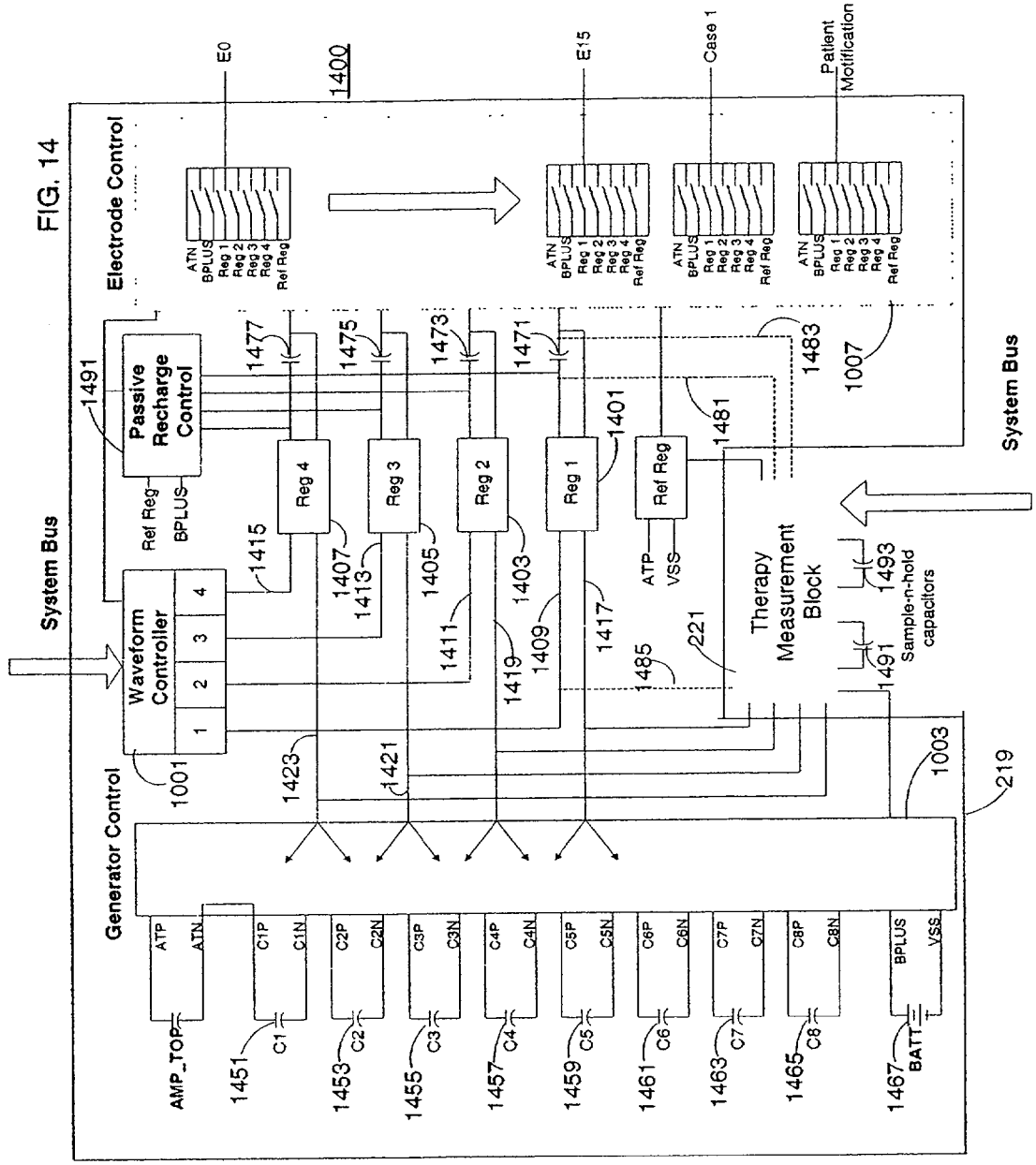

AUTOMATIC WAVEFORM OUTPUT ADJUSTMENT FOR AN IMPLANTABLE MEDICAL DEVICE

FIELD OF THE INVENTION

This invention relates generally to implantable medical devices, and more particularly to the generation of stimulation pulses for implantable medical devices.

BACKGROUND OF THE INVENTION

This disclosure relates to a medical device and more specifically to an implantable neuro stimulator that produces an electrical stimulation signal used to influence the human body.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. One type of medical device that can be used is an Implantable Neuro Stimulator (INS).

An INS generates an electrical stimulation signal that is used to influence the human nervous system or organs. Electrical contacts carried on the distal end of a lead are placed at the desired stimulation site such as the spine and the proximal end of the lead is connected to the INS. The INS is then surgically implanted into an individual such as into a subcutaneous pocket in the abdomen. The INS can be powered by an internal source such as a battery or by an external source such as a radio frequency transmitter. A clinician programs the INS with a therapy using a programmer. The therapy configures parameters of the stimulation signal for the specific patient's therapy. An INS can be used to treat conditions such as pain, incontinence, movement disorders such as epilepsy and Parkinson's disease, and sleep apnea Additional therapies appear promising to treat a variety of physiological, psychological, and emotional conditions. As the number of INS therapies has expanded, greater demands have been placed on the INS. Examples of some INSs and related components are shown and described in a brochure titled Implantable Neurostimulation Systems available from Medtronic, Inc., Minneapolis, Minn.

The effectiveness of the therapy as provided by the INS is dependent upon adjusting the electrical characteristics of the stimulation signal. For example, stimulation waveforms can be designed for selective electrical stimulation of the nervous system. Two types of selectivity may be considered. First, fiber diameter selectivity refers to the ability to activate one group of nerve fibers having a common diameter without activating nerve fibers having different diameters. Second, spatial selectivity refers to the ability to activate nerve fibers in a localized region without activating nerve fibers in neighboring regions.

The clinician may consider a number of factors such as the type of disorder and the specific condition of the patient in order to determine the electrical characteristics of the stimulation waveform When the INS has been configured by the clinician, it is important that the INS provides continued operation in accordance with the configuration However, the battery voltage may change with the continued powering of the INS. Also, components of the INS may fail, causing the electrical characteristics of the stimulation waveform to change. Thus, apparatus and method that help in assuring the electrical characteristics of a stimulation waveform is of importance in advancing the field of Implantable Neurological Stimulators.

BRIEF SUMMARY OF THE INVENTION

In an embodiment of the invention, apparatus and method assure the electrical characteristics of a stimulation waveform to an electrode of an Implantable Neuro Stimulator (INS). The embodiment comprises a regulator, a measurement module, a generator, and a processor. The generator provides an input signal to the regulator. The regulator consequently regulates the input signal in order to form a pulse that is applied to the electrode. The processor instructs the measurement module to perform an electrical measurement that is indicative of an amplitude of the pulse. If the electrical measurement is sufficiently different from a desired value, the processor instructs the generator to be reconfigured in order that the amplitude of the pulse is within an acceptable value. With the embodiment, a redundant capacitor pair may be inserted in a capacitor arrangement in order to compensate for a reduced battery voltage.

With another embodiment of the invention, a detected faulty component such as a capacitor or a regulator may be replaced with a redundant component. If a redundant component is not available, the processor notifies the clinician through a programmer about the out-of regulator condition. The regulator may instruct the INS to shutdown in order to suspend the generation of a stimulation waveform that is not within an acceptable range.

BRIEF DESCRIPTION OF THE DRAWINGS

FIG. 1 shows an environment of an exemplary Implantable Neuro Stimulator (INS);

FIG. 14 shows a stimulation engine system according to an embodiment of the present invention;

DETAILED DESCRIPTION OF THE INVENTION

Figure 2:
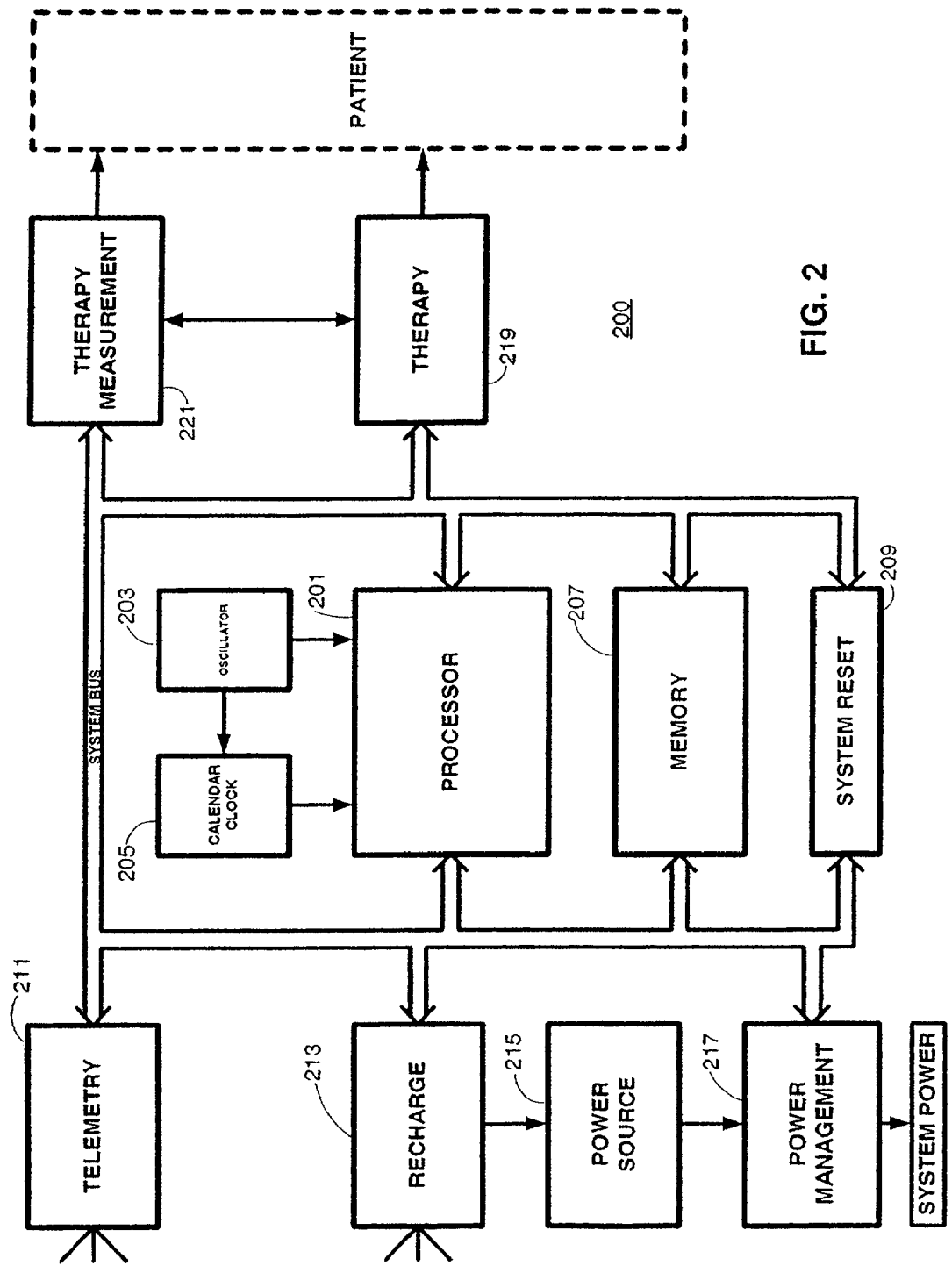
FIG. 2 shows an INS block diagram.

Overall Implantable Medical Device System. FIG. 1 shows the general environment of an Implantable Neuro Stimulator (INS) medical device 14 in accordance with a preferred embodiment of the present invention. The neurostimulation system generally includes an INS 14, a lead 12, a lead extension 20, an External Neuro Stimulator (ENS) 25, a physician programmer 30, and a patient programmer 35. The INS 14 preferably is a implantable pulse generator that will be available from Medtronic, Inc. with provisions for multiple pulses occurring either simultaneously or with one pulse shifted in time with respect to the other, and having independently varying amplitudes and pulse widths. The INS 14 contains a power source and electronics to send precise, electrical pulses to the spinal cord, brain, or neural tissue to provide the desired treatment therapy. In the embodiment, INS 14 provides electrical stimulation by way of pulses although alternative embodiments may use other forms of stimulation such as continuous electrical stimulation.

The lead 12 is a small medical wire with special insulation. The lead 12 includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 12 may also be a paddle having a plurality of electrodes including, for example, a Medtronic paddle having model number 3587A. Those skilled in the art will appreciate that any variety of leads may be used to practice the present invention.

The lead 12 is implanted and positioned to stimulate a specific site in the spinal cord or the brain. Alternatively, the lead 12 may be positioned along a peripheral nerve or adjacent neural tissue ganglia like the sympathetic chain or it may be positioned to stimulate muscle tissue. The lead 12 contains one or more electrodes (small electrical contacts) through which electrical stimulation is delivered from the INS 14 to the targeted neural tissue. If the spinal cord is to be stimulated, the lead 12 may have electrodes that are epidural, intrathecal or placed into the spinal cord itself. Effective spinal cord stimulation may be achieved by any of these lead placements.

Although the lead connector can be connected directly to the INS 14, typically the lead connector is connected to a lead extension 20 which can be either temporary for use with an ENS 25 or permanent for use with an INS 14. An example of the lead extension 20 is Model 7495 available from Medtronic.

The ENS 25 functions similarly to the INS 14 but is not designed for implantation. The ENS 25 is used to test the efficacy of stimulation therapy for the patient before the INS 14 is surgically implanted. An example of an ENS 25 is a Model 3625 Screener available from Medtronic.

The physician programmer 30, also known as a console programmer, uses telemetry to communicate with the implanted INS 14, so a physician can program and manage a patient's therapy stored in the INS 14 and troubleshoot the patient's INS system. An example of a physician programmer 30 is a Model 7432 Console Programmer available from Medtronic. The patient programmer 35 also uses telemetry to communicate with the INS 14, so the patient can manage some aspects of her therapy as defined by the physician. An example of a patient programmer 35 is a Model 7434 Itrel® EZ Patient Programmer available from Medtronic.

Those skilled in the art will appreciate that any number of external programmers, leads, lead extensions, and INSs may be used to practice the present invention.

Implantation of an Implantable Neuro Stimulator (INS) typically begins with implantation of at least one stimulation lead 12 usually while the patient is under a local anesthetic. The lead 12 can either be percutaneously or surgically implanted. Once the lead 12 has been implanted and positioned, the lead's distal end is typically anchored into position to minimize movement of the lead 12 after implantation. The lead's proximal end can be configured to connect to a lead extension 20. If a trial screening period is desired, the temporary lead extension 20 can be connected to a percutaneous extension with a proximal end that is external to the body and configured to connect to an External Neuro Stimulator (ENS) 25. During the screening period the ENS 25 is programmed with a therapy and the therapy is often modified to optimize the therapy for the patient. Once screening has been completed and efficacy has been established or if screening is not desired, the lead's proximal end or the lead extension proximal end is connected to the INS 14. The INS 14 is programmed with a therapy and then implanted in the body typically in a subcutaneous pocket at a site selected after considering physician and patient preferences. The INS 14 is implanted subcutaneously in a human body and is typically implanted near the abdomen of the patient.

System Components and Component Operation. FIG. 2 shows a block diagram of an exemplary INS 200. INS 200 generates a programmable electrical stimulation signal. INS 200 comprises a processor 201 with an oscillator 203, a calendar clock 205, a memory 207, a system reset module 209, a telemetry module 211, a recharge module 213, a power source 215, a power management module 217, a therapy module 219, and a therapy measurement module 221. In non-rechargeable versions of INS 200, recharge module 213 can be omitted. Other versions of INS 200 can include additional modules such as a diagnostics module. All components can be configured on one or more Application Specific Integrated Circuits (ASICs) except the power source. Also, all components are connected to bi-directional data bus that is non-multiplexed with separate address and data lines except oscillator 203, calendar clock 205, and power source 215. Other embodiments may multiplex the address and data lines. Processor 201 is synchronous and operates on low power such as a Motorola 68HC11 synthesized core operating with a compatible instruction set. Oscillator 203 operates at a frequency compatible with processor 201, associated components, and energy constraints such as in the range from 100 KHz to 1.0 MHz. Calendar clock 205 counts the number of seconds since a fixed date for date/time stamping of events and for therapy control such as circadian rhythm linked therapies. Memory 207 includes memory sufficient for operation of the INS such as volatile Random Access Memory (RAM) for example Static RAM, nonvolatile Read Only Memory (ROM), Electrically Eraseable Programmable Read Only Memory (EEPROM) for example Flash EEPROM, and register arrays configured on ASICs. Direct Memory Access (DMA) is available to selected modules such as telemetry module 211, so telemetry module 211 can request control of the data bus and write data directly to memory bypassing processor 201. System reset module 209 controls operation of ASICs and modules during power-up of INS 200, so ASICs and modules registers can be loaded and brought on-line in a stable condition. INS 200 can be configured in a variety of versions by removing modules not necessary for the particular configuration and by adding additional components or modules. Primary cell, non-rechargeable versions of INS 200 will not include some or all of the components in the recharge module. All components of INS 200 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones.

Figure 3:
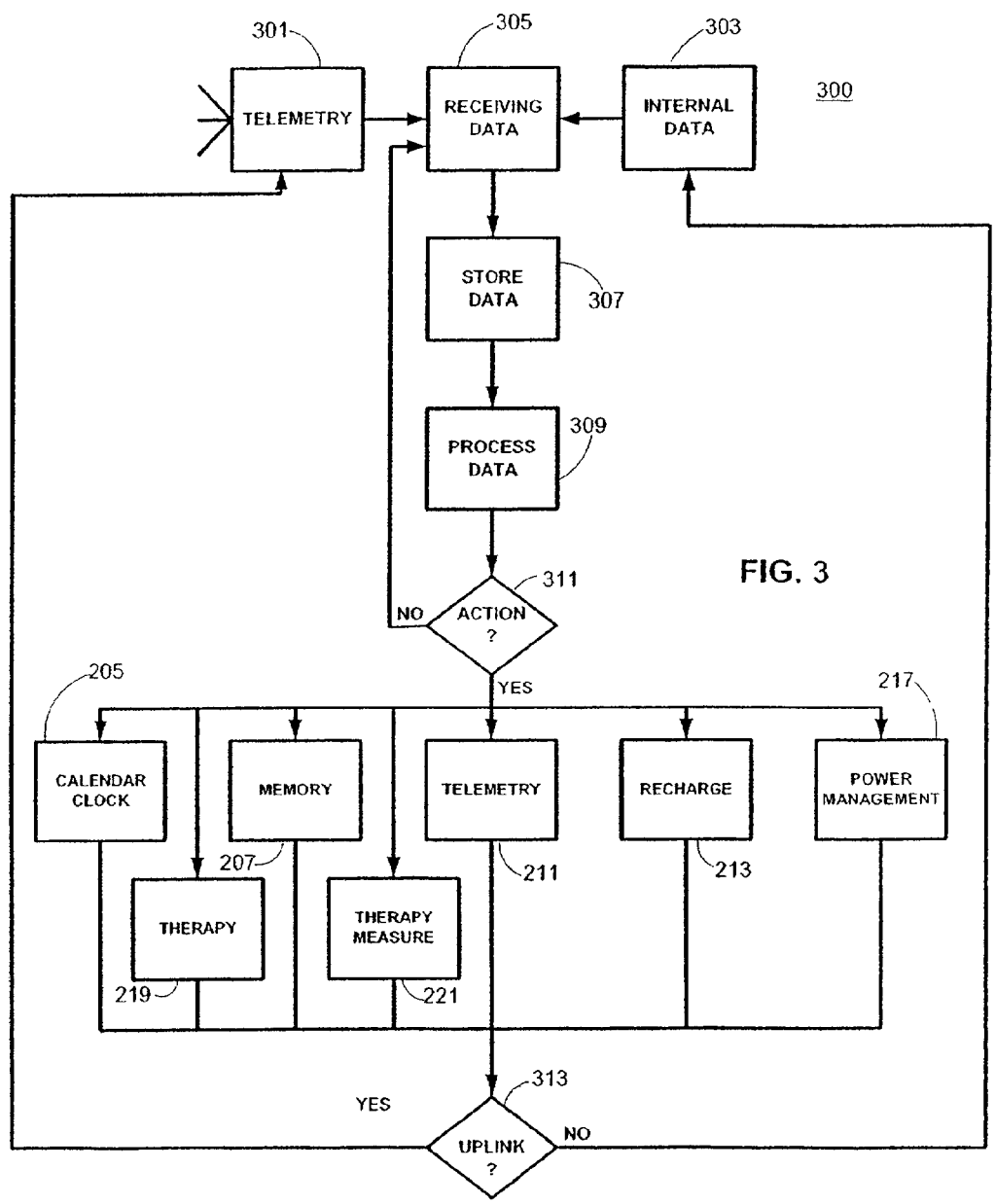
FIG. 3 shows an INS basic operation flowchart.

FIG. 3 illustrates an example of a basic INS operation flowchart 300. Operation begins with when processor 201 receives data from either telemetry 301 or from an internal source 303 in INS 200. At receiving data step 305, received date is then stored in a memory location 307. The data 307 is processed by processor 201 in step 309 to identify the type of data and can include further processing such as validating the integrity of the data. After data 307 is processed, a decision is made whether to take an action in step 311. If no action is required, INS 201 stands by to receive data If an action is required, the action will involve one or more of the following modules or components: calendar clock 205, memory 207, telemetry 211, recharge 213, power management 217, therapy 219, and therapy measurement 221. An example of an action would be to modify a programmed therapy. After the action is taken, a decision is made whether to prepare the action to be communicated in step 313, known as uplinked, to patient programmer 35 or console programmer 30 through telemetry module 211. If the action is uplinked, the action is recorded in patient programmer 35 or console programmer 30. If the action is not uplinked, the action is recorded internally within INS 200.

Figure 4:
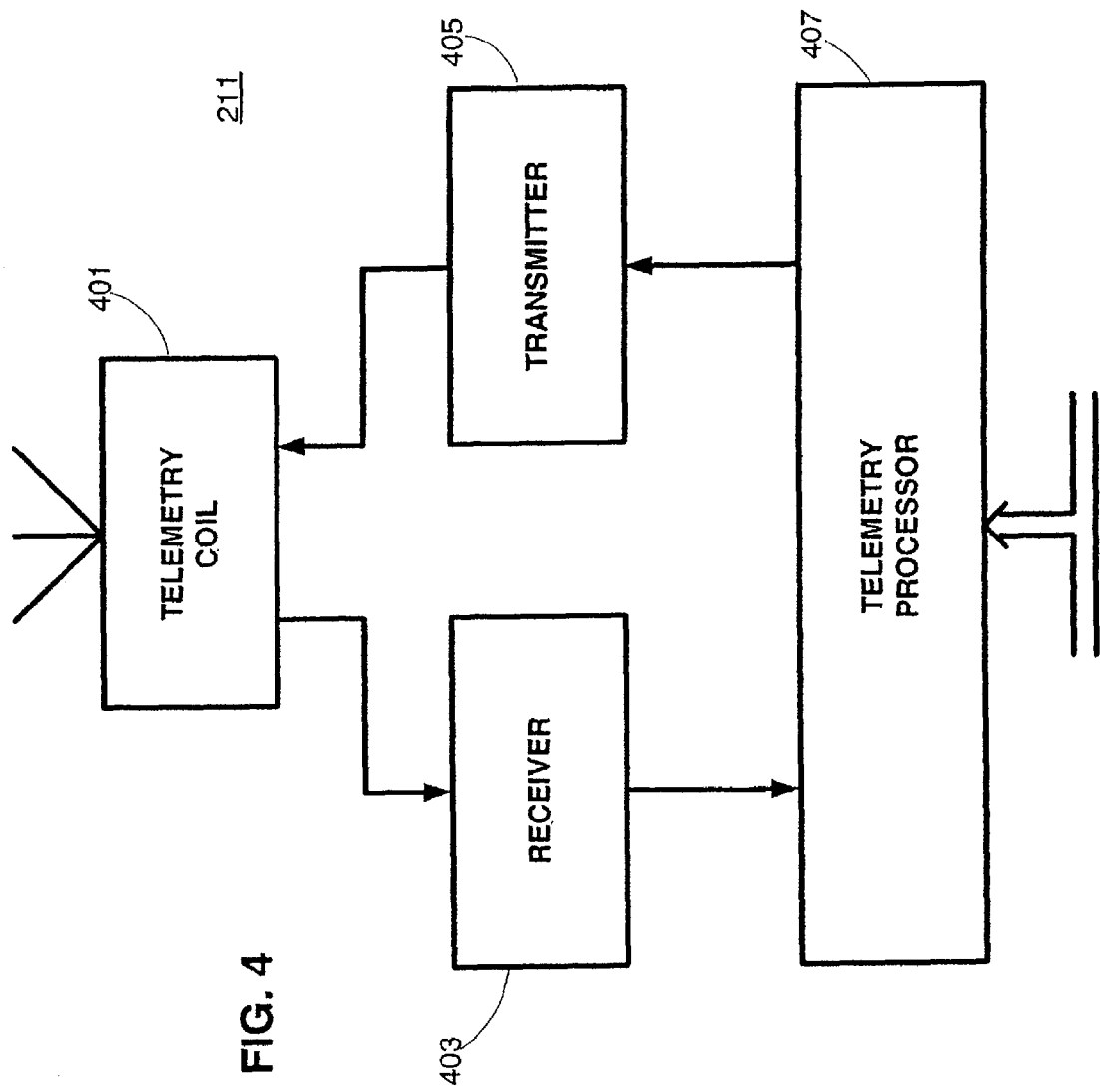
FIG. 4 shows a telemetry module block diagram.

FIG. 4 shows a block diagram of various components that may be found within telemetry module 211. Telemetry module 211 provides bi-directional communications between INS 200 and the programmers. Telemetry module 211 comprises a telemetry coil 401, a receiver 403, a transmitter 405, and a telemetry processor 407. Telemetry is conducted at a frequency in the range from about 150 KHz to 200 KHz using a medical device protocol such as described in U.S. Pat. No. 5,752,977 entitled "Efficient High Data Rate Telemetry Format For Implanted Medical Device" issued on May 19, 1998 and having named inventors Grevious et al. Telemetry coil 401 can be located inside the housing or attached to the outside of the housing, and telemetry coil 401 can also function as the recharge coil if operation of the coil is shared or multiplexed. Receiver 403 processes a digital pulse representing the Radio Frequency (RF) modulated signal, knows as a downlink, from a programmer. Transmitter 405 generates an RF modulated uplink signal from the digital signal generated by telemetry processor 407. Telemetry processor 407 may be a state machine configured on an ASIC with the logic necessary to decode telemetry signal during reception, store data into RAM, and notify processor 201 that data was received. Telemetry processor 407 also provides the logic necessary during transmission to request processor 201 to read data from RAM, encode the data for transmission, and notify the process that the data was transmitted. Telemetry processor 407 reduces some demands on processor 201 in order to save energy and enable processor 201 to be available for other functions.

Figure 5:
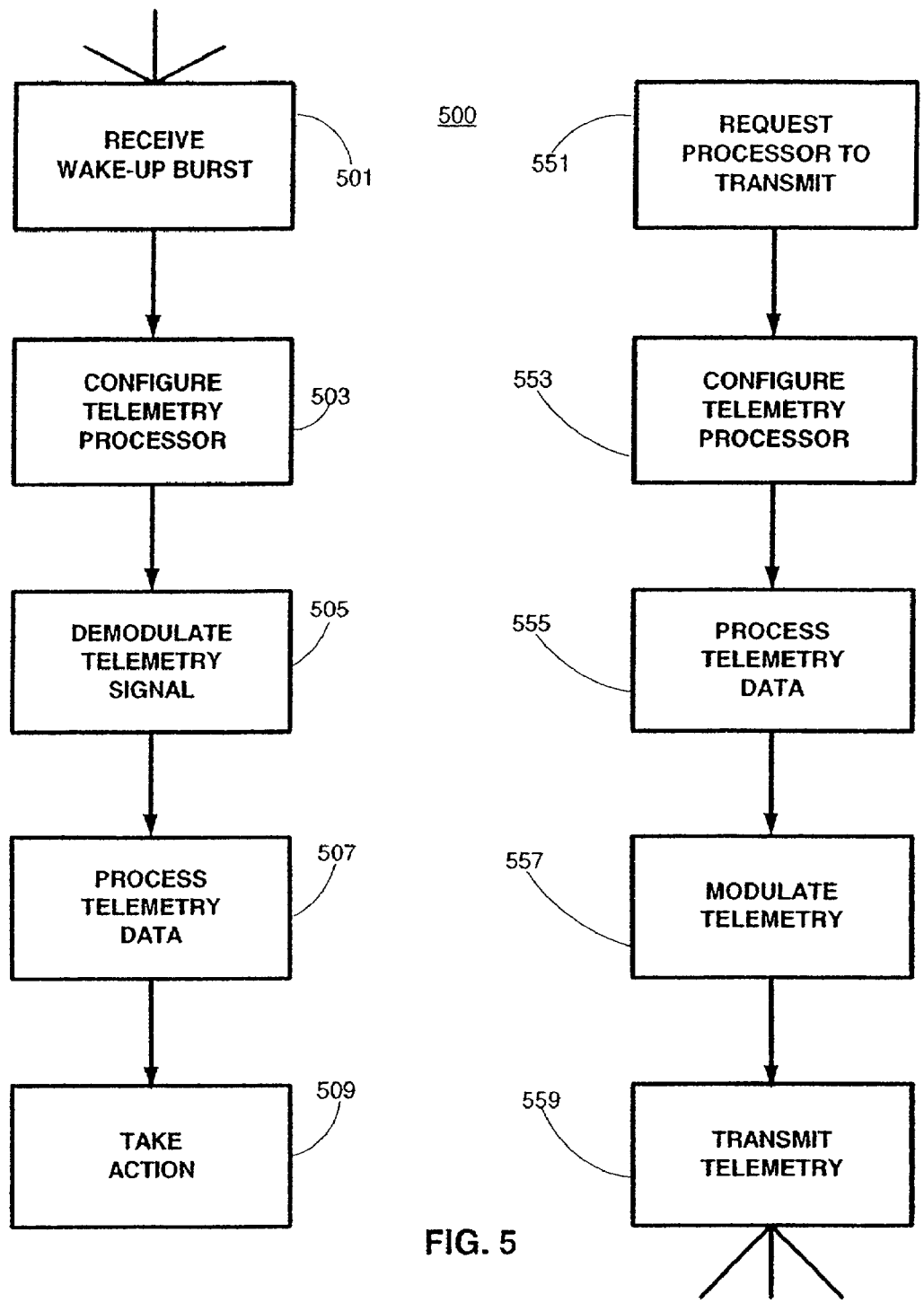
FIG. 5 shows a telemetry operation flowchart.

FIG. 5 illustrates an example of a telemetry operation flowchart 500. To begin telemetry, either the patient or the clinician uses patient programmer 35 or console programmer 30 and places the telemetry head containing telemetry coil 401 near INS 200 or the ENS. In step 501, the RF telemetry signal is received through telemetry coil 401 and includes a wake-up burst that signals telemetry processor 407 to prepare telemetry processor 407 to receive incoming telemetry signals. Telemetry processor 407 is configured to receive a particular telemetry protocol that includes the type of telemetry modulation and the transmission rate of the incoming telemetry signal in step 503. Telemetry receiver 403 demodulates the time base signal into digital pulses in step 505. Telemetry processor 407 converts the digital pulses into binary data that is stored into memory. In step 509, processor 201 will then take whatever action is directed by the received telemetry such as adjusting the therapy. Telemetry signal transmission is initiated by processor 201 requesting telemetry processor 407 to transmit data in step 551. Telemetry processor 407 is configured for the desired telemetry protocol that includes the type of modulation and the speed for transmission in step 553. Telemetry processor 407 converts the binary data into a time based digital pulses in step 555. Transmitter 405 modulates the digital signal into an RF signal that is then transmitted through telemetry coil 401 to programmer 30 or 35 in step 559.

Figure 6:
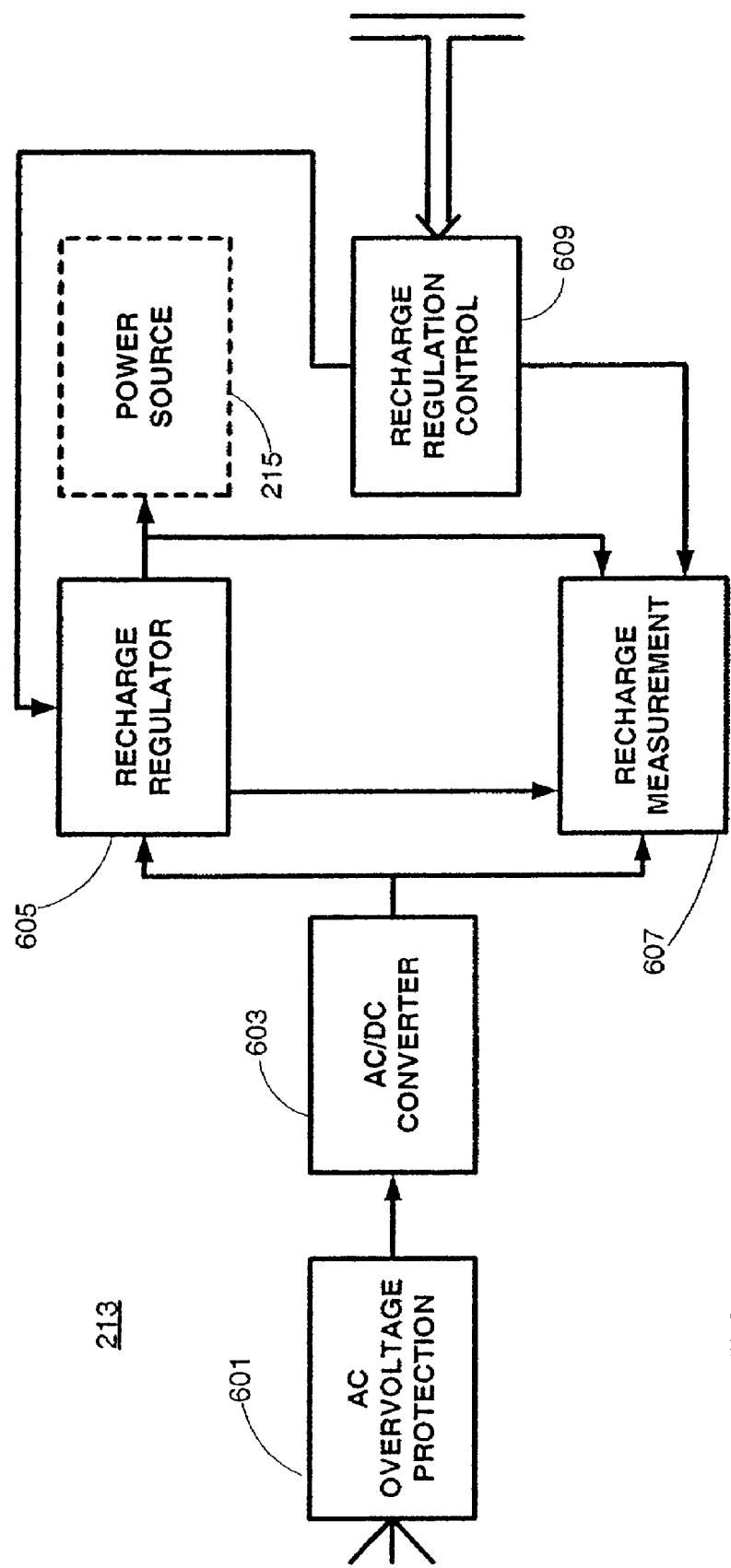
FIG. 6 shows a recharge module block diagram.

FIG. 6 shows a block diagram of various components that may be found within recharge module 213. Recharge module 213 provides controlled power to the battery (contained in power source 215) for recharging the battery and provides information to INS 200 about recharging status. Recharge module 213 regulates the charging rate of power source 215 according to power source parameters and keeps the temperature rise of INS 200 within acceptable limits so that the temperature rise does not create an unsafe condition for the patient. INS 200 communicates charging status to the patient's charger (213), so the patient charges at a level that prevents INS 200 from overheating while charges power source 215 rapidly. Recharge module 213 comprises a recharge coil, an Alternating Current (AC) over-voltage protection unit 601, an AC to DC converter 603, a recharge regulator 605, a recharge measurement unit 607, and a recharge regulator control 609. Recharge module 213 charges the battery by receiving a power transfer signal with a frequency of about 5.0 KHz to 10.0 KHz and converting the power transfer signal into a regulated DC power that is used to charge the battery. The recharge coil can be the same coil as telemetry coil 401 if shared or multiplexed or the recharge coil can be a separate coil. AC over-voltage protection unit 601 can be a Zener diode that shunts high voltage to ground. AC to DC converter 603 can be a standard rectifier circuit. Recharge regulator 605 regulates the voltage received from AC to DC converter 603 to a level appropriate for charging the battery. The recharge regulator control adjusts recharge regulator 605 in response to recharge measurements and a recharge program. The recharge program can vary based upon the type of device, type of battery, and condition of the battery. The recharge measurement block 607 measures current and voltage at regulator 605. Based upon the recharge measurement, the regulation control can increase or decrease the power reaching power source 215.

Figure 7:
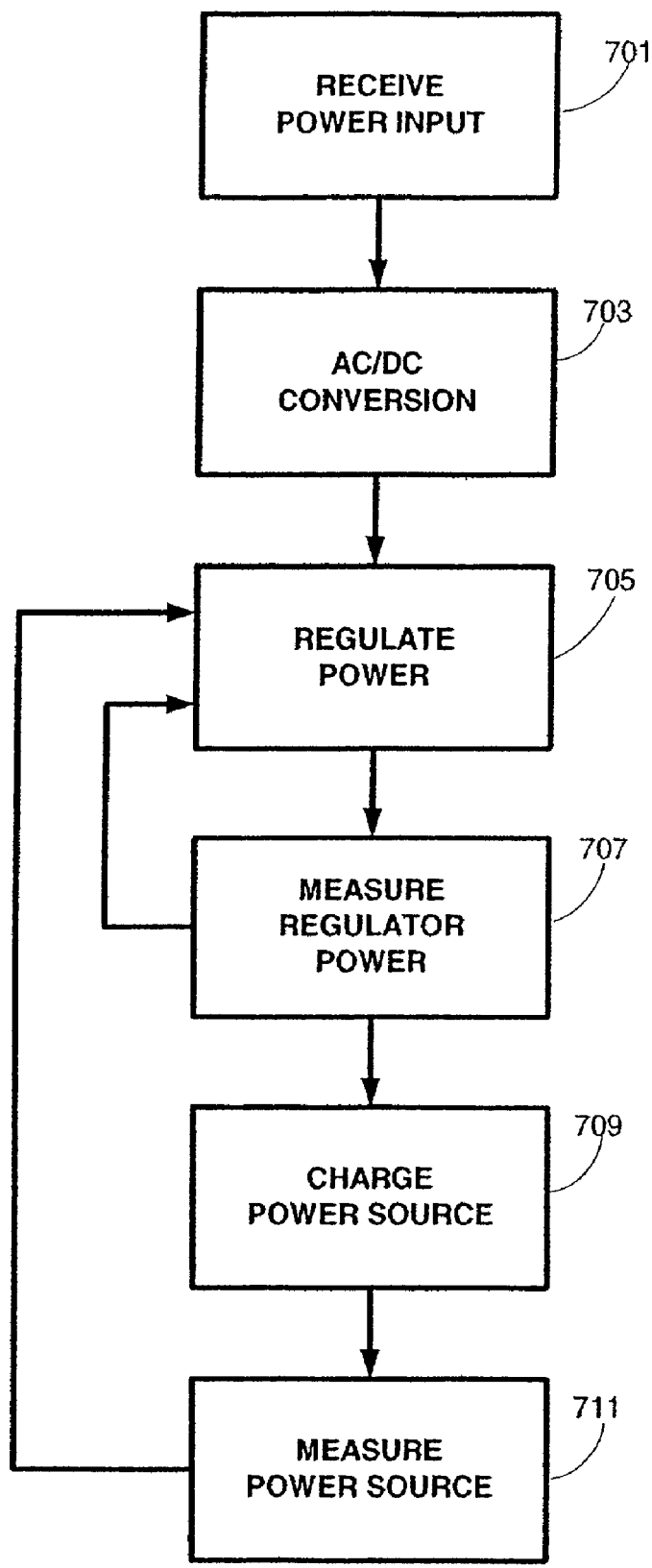
FIG. 7 shows a recharge module operation flowchart.

FIG. 7 illustrates an example of recharge module operation flowchart corresponding to recharge module 213. Recharging INS 200 begins in the same manner as telemetry with either the patient or the clinician using patient programmer 35 or console programmer 30 and placing the telemetry head containing the recharge coil near INS 200 or the ENS. After the recharge signal is received in step 701, it is converted to from AC to DC in step 703. The DC signal is regulated in step 707. Regulator output power is measured in step 707 and then fed back in step 705 in order to assist in controlling the regulator output power to an appropriate power level. Power source 215 is charged in step 709, and the power source charge level is measured in step 711. The measured power source charge level also is fed back in step 705, so regulator 605 can control the regulator output to a level that is appropriate for power source 215. Once recharge module 213 fully charges power source 215, recharge module 213 can be configured to function as a power source for INS 200 while power is still received.

Figure 8:
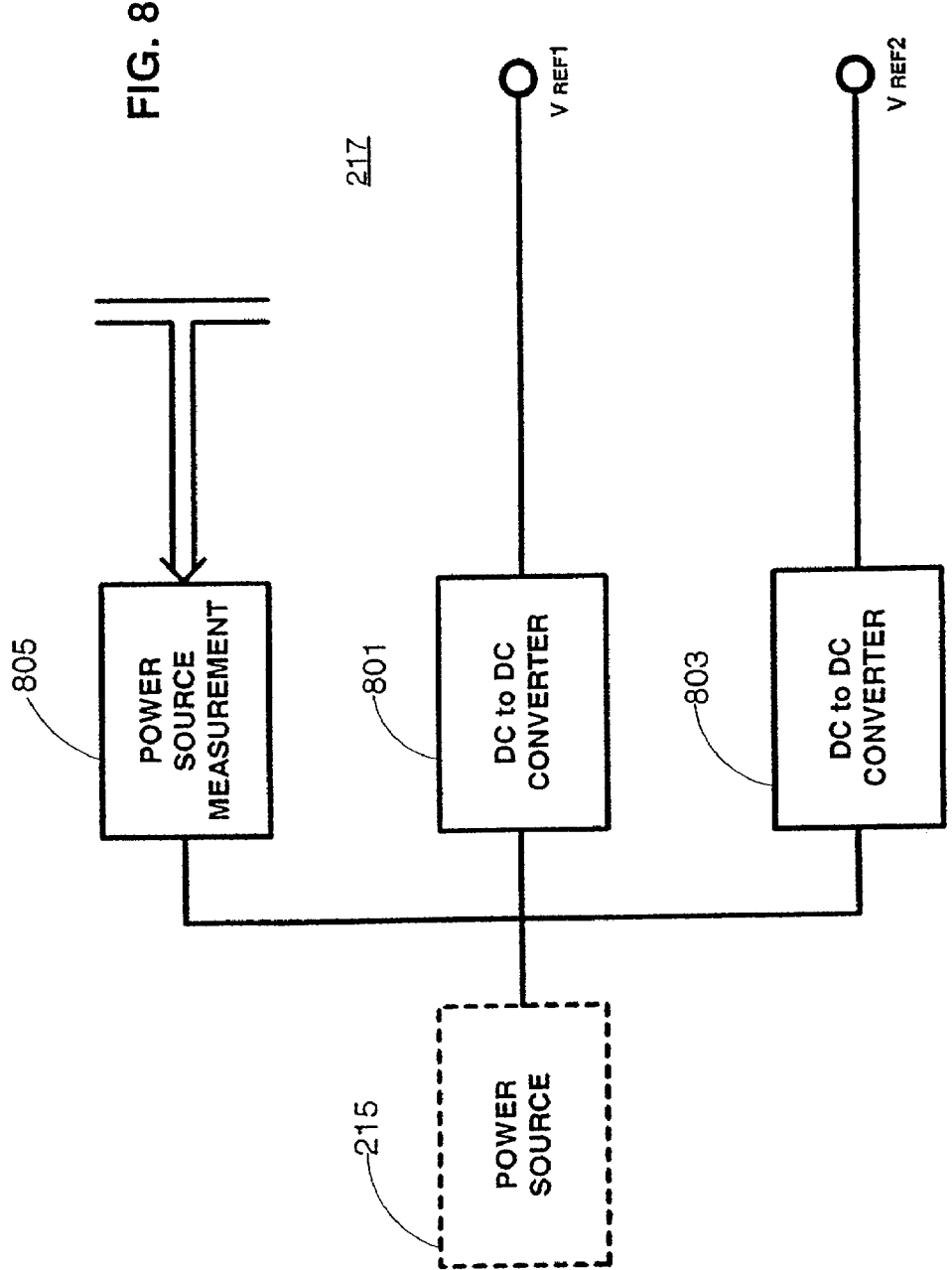
FIG. 8 shows a power module block diagram.
Figure 9:
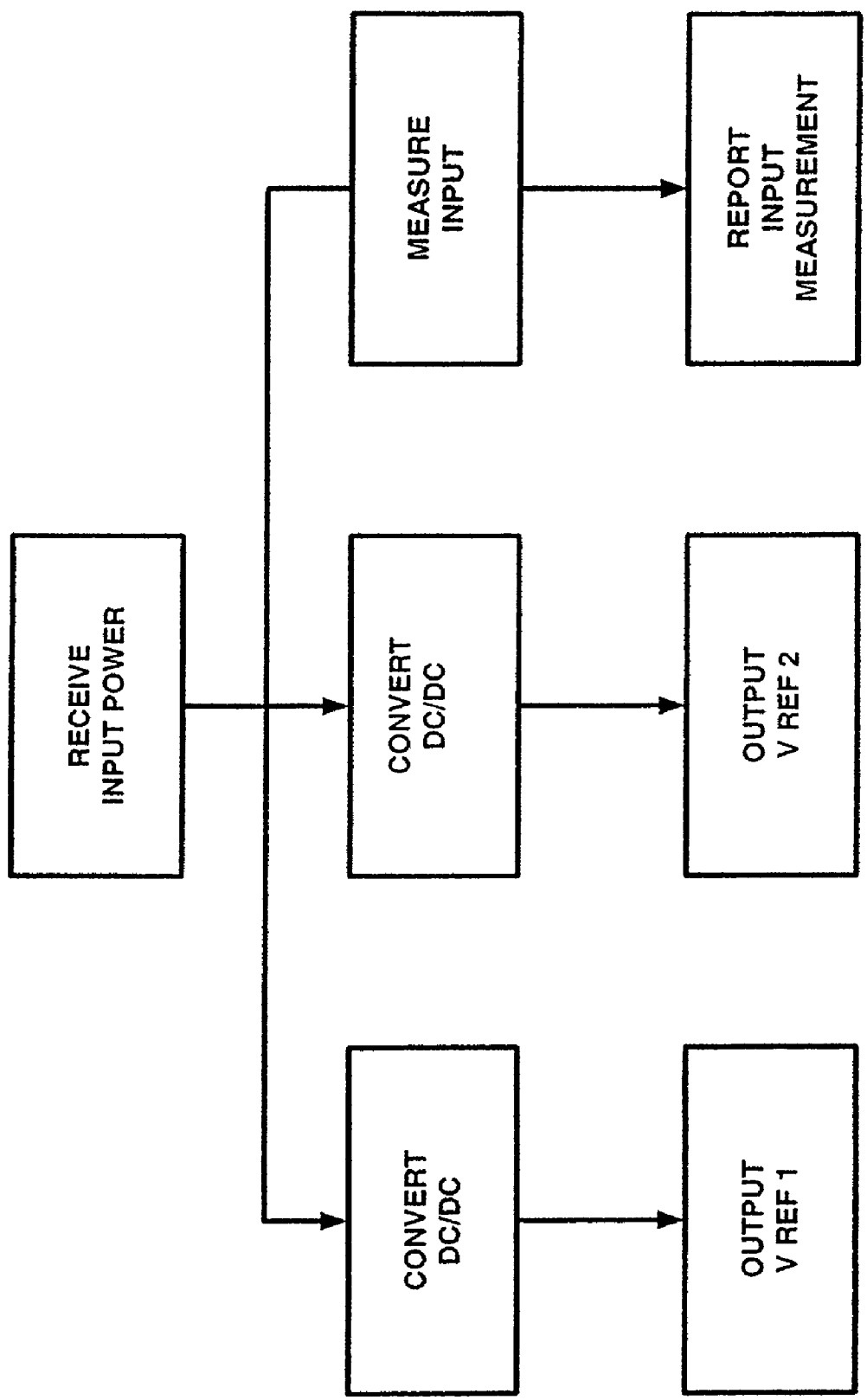
FIG. 9 shows power module operation flowchart.

FIG. 8 shows a block diagram of various components that may be found within power management module 217, and FIG. 9 illustrates an example of a flowchart of power management module 217. Power management module 217 provides a stable DC power source to INS 200 with voltages sufficient to operate INS 200 such as between about 1.5 VDC and 2.0 VDC. Power management module 217 includes a first DC to DC converter 801, a second DC to DC converter 803, and power source measurement component 805. One or more additional DC to DC converters can be added to the power management module to provide additional voltage values for INS 200. First DC to DC converter 801 and second DC to DC converter 803 can be operational amplifiers configured for a gain necessary for the desired output voltage. Power source measurement component 805 measures the power source and reports this measurement to processor 201, so processor 201 can determine information about power source 215. If processor 201 determines that power source 215 is inadequate for normal operation, processor 201 can instruct power management module 217 to initiate a controlled shutdown of INS 200.

INS power source 215 typically provides a voltage sufficient for power management module 217 to supply power to INS 200 such as above 2.0 VDC at a current in the range from about 5.0 mA to 30.0 mA for a time period adequate for the intended therapy. INS power source 215 can be a physical storage source such as a capacitor or super capacitor, or power source 215 can be a chemical storage source such as a battery. The INS battery can be a hermetically sealed rechargeable battery such as a lithium ion (Li+) battery or a non-rechargeable battery such as a lithium thionyl chloride battery. The ENS battery can be a non-hermetically sealed rechargeable battery such as nickel cadmium or anon-rechargeable battery such as an alkaline.

Figure 10:
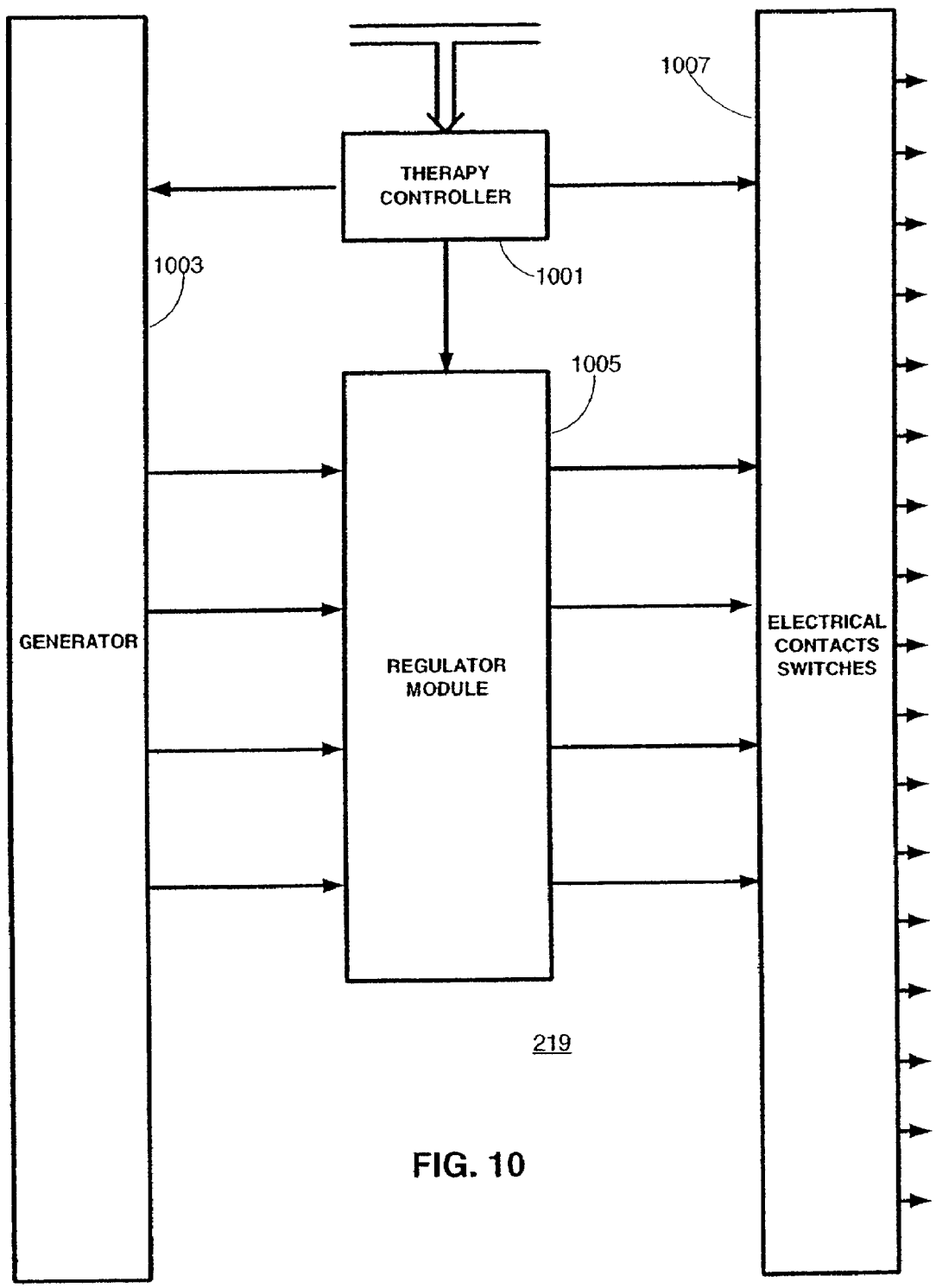
FIG. 10 shows a therapy module block diagram.

FIG. 10 shows a block diagram of various components that may be found within therapy module 219. Therapy module 219 generates a programmable stimulation signal that is transmitted through one or more leads to electrical contacts implanted in the patient. Therapy module 219 comprises a therapy controller (waveform controller) 1001, a generator 1003, a regulator module 1005, and an electrical contact switches unit 1007. Therapy controller 1001 can be a state machine having registers and a timer. Other embodiments of the invention may utilize other types of processors such as an ASIC, a microprocessor, a gate array, and discrete circuitry. Therapy controller 1001 controls generator 1003 and regulator module 1005 to create a stimulation signal. (A waveform generator that forms the stimulation signal may comprise generator 1003 and regulator module 1005.) Generator 1003 assembles capacitors that have been charged by power source 215 to generate a wide variety of voltages or currents. Regulator module 1005 includes current/voltage regulators that receive a therapy current or voltage from generator 1003 and shape the stimulation signal according to therapy controller 1001. Regulator module 1005 may include any number of devices or software components (active or passive) that maintains an output within a range of predetermined parameters such as current, voltage, etc. Electrical contact switches unit comprises solid state switches with low impedance such as Field Effect Transistor (FET) switches. The electrical contacts are carried on the distal end of a lead and deliver the stimulation signal to the body through an electrode. Additional switches can be added to provide a stimulation signal to additional electrical contacts. In the embodiment, therapy module 219 can deliver individual output pulses in the range from 0.0 Volts to 15.0 Volts into a range from about 1.0 Ohm to 10.0 K Ohms impedance throughout its operating parameter range to any combination of anodes and cathodes of up to eighteen electrical contacts for any given stimulation signal. Other embodiments can support a different voltage range, a different impedance range, or a different electrode arrangement.

Figure 11:
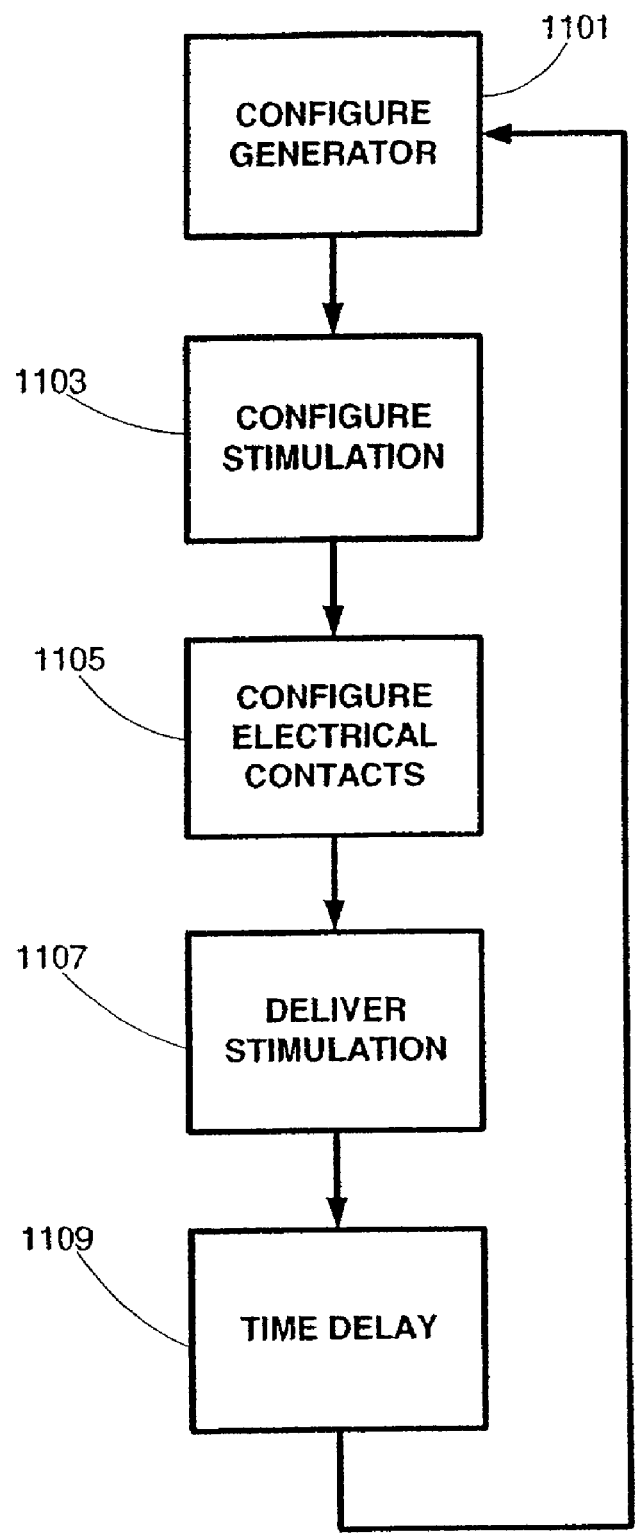
FIG. 11 shows a therapy module operation flowchart.

FIG. 11 illustrates and example of operation with a flowchart of therapy module 219. The therapy begins with the therapy controller 1001 configuring the generator 1003 according to the therapy program to provide appropriate voltage to regulator module 1005 in step 1101. Therapy controller 1001 also configures regulator module 1005 to produce the stimulation signal according to the therapy program in step 1103. Therapy controller 1001 also configures electrical contacts unit 1007 to so the stimulation signal is delivered to the electrical contacts specified by the therapy program in step 1105. The stimulation signal is delivered to the patient through electrodes in step 1107. After the stimulation signal is delivered to the patient, most therapies include a time delay in step 1109 before the next stimulation signal is delivered.

Figure 12:
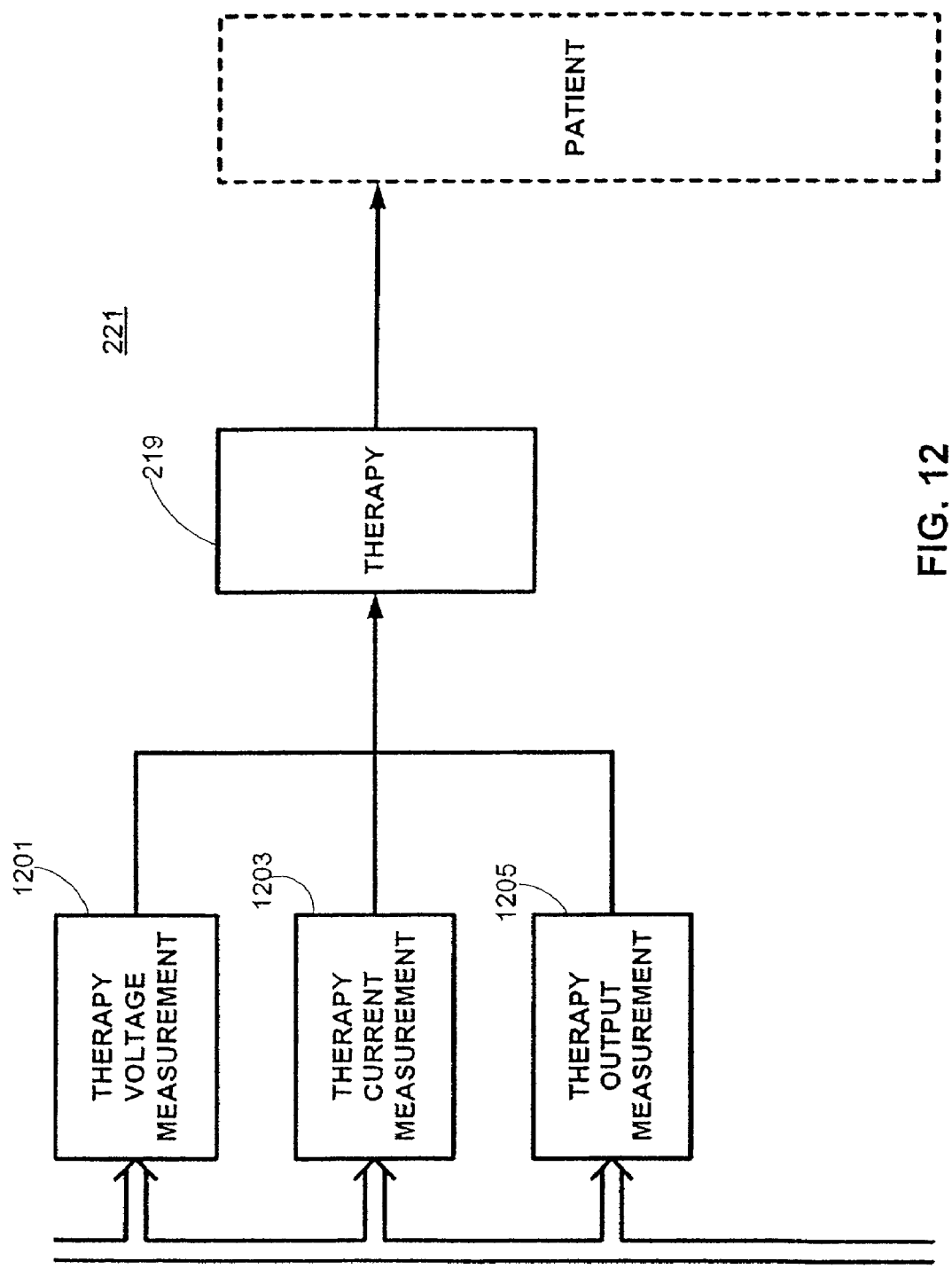
FIG. 12 shows a therapy measurement module block diagram.

FIG. 12 shows a block diagram of various components that may be found within therapy measurement module 221. Therapy measurement module 221 measures one or more therapy parameters at therapy module 219 to determine whether the therapy is appropriate. Therapy measurement module 221 includes a therapy voltage measurement component 1201, a therapy current measurement component 1203, and a therapy output measurement component 1205. The therapy voltage measurements and therapy current measurements are taken periodically to perform therapy calculations. The therapy output measurement is a measurement of the delivered therapy that is used for safety and other purposes.

Figure 13:
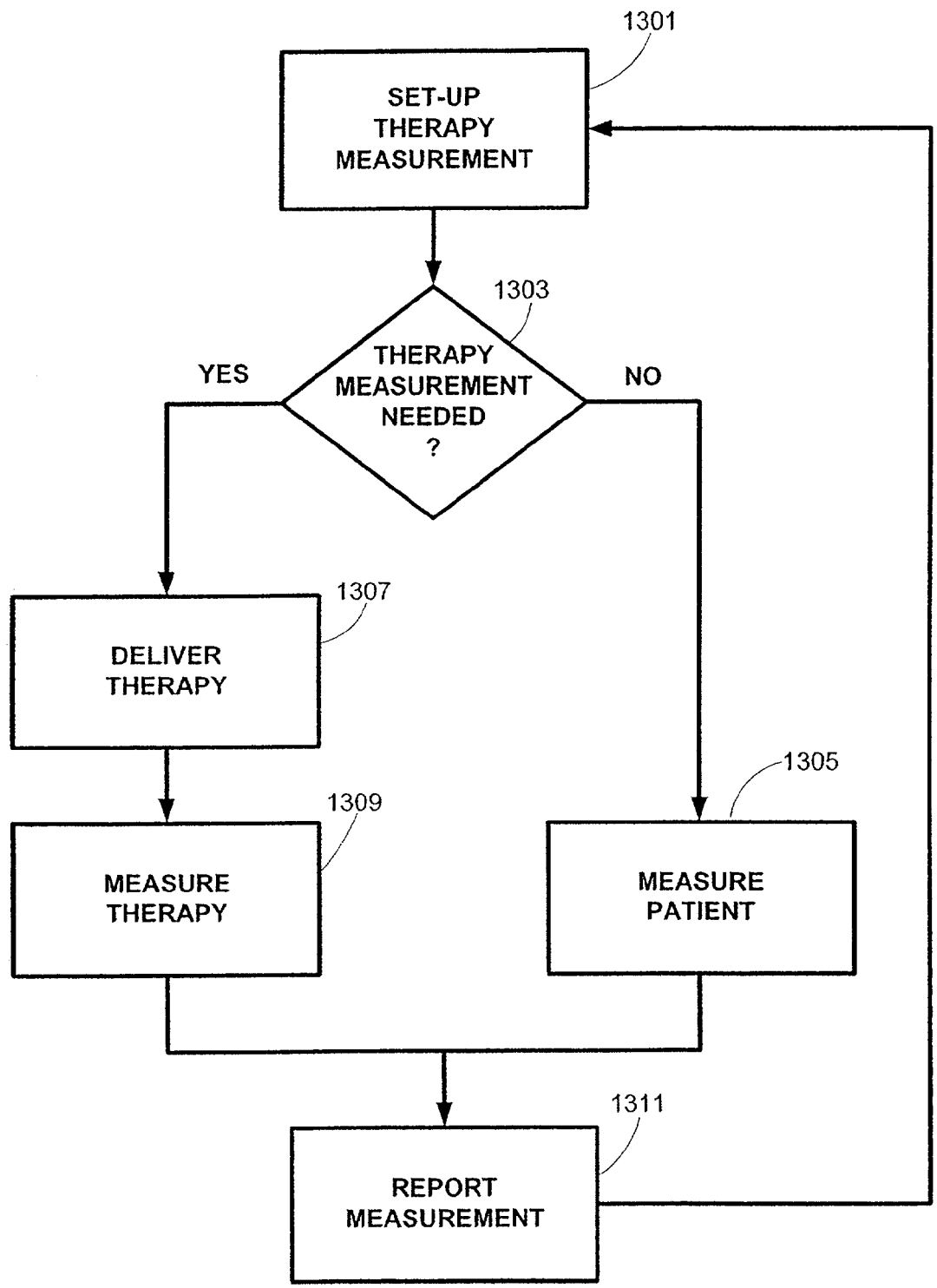
FIG. 13 shows a therapy measurement module operation flowchart.

FIG. 13 illustrates an example of an operation flowchart of therapy measurement module 221. In step 1301, the therapy measurement operation begins by processor 201 setting up parameters of the therapy measurement to be taken (e.g. the specific stimulation signal to measure) and at which electrical contacts to perform the measurement. Before a therapy measurement is taken, a threshold determination is made whether a therapy measurement is needed in step 1303. For some therapies, a therapy measurement may not be taken. When a therapy measurement is not taken, often a patient physiological measurement will be performed and reported to processor 201 for action or storage in memory in step 1305. When a therapy measurement is desired, the therapy is delivered in step 1307 and then the therapy measurement is performed in step 1309. The therapy measurement is reported to processor 201 for action or storage in memory in step 1311. Examples of some actions that might be taken when the therapy measurement is reported include an adjustment to the therapy and a diary entry in memory that can be evaluated by the clinician at a later time.

Those skilled in the art will appreciate that the above discussion relating to the operation and components of the INS 14 serve as an example and that other embodiments may be utilized and still be considered to be within the scope of the present invention. For example, an ENS 25 may be utilized with the present invention.

Figure 19:
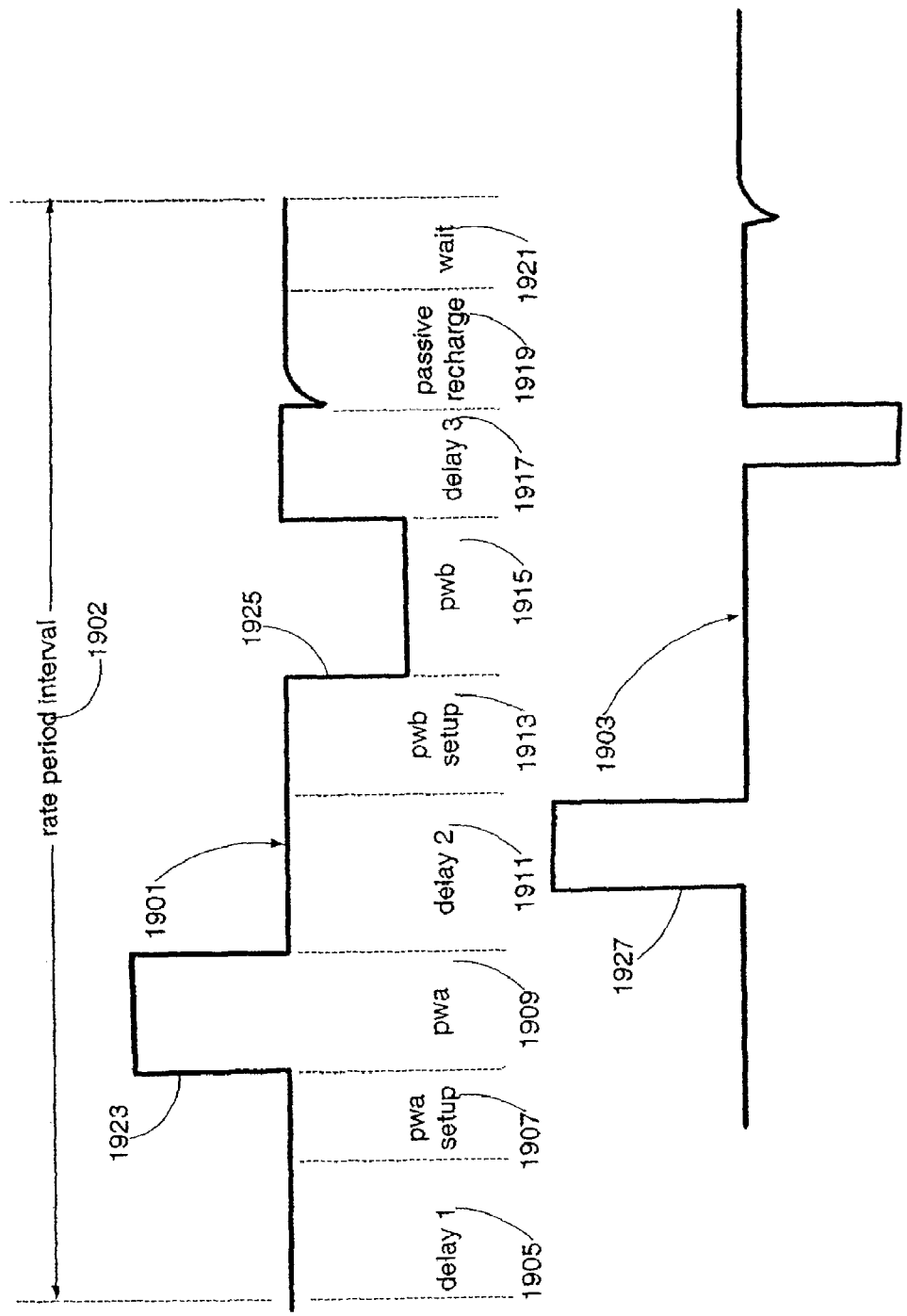
FIG. 19 shows a stimulation waveform according to an embodiment of the present invention.

Stimulation Engine. FIG. 14 shows a stimulation engine system 1400 according to an embodiment of the present invention. Stimulation engine 1400 comprises therapy module 219 and therapy measurement block 221. Therapy module 219 comprises generator control module 1003, waveform controller (therapy controller) 1001, regulators 1401, 1403, 1405, and 1407, and electrode controller (electrical contact switches unit) 1007. Regulators 1401–1407 receive an input voltage from a capacitor bank comprising capacitors 1451–1465. In the embodiment, capacitors 1451–1465 are associated as capacitor pairs such as described in U.S. Pat. No. 5,948,004 entitled "Implantable Stimulation Having An Efficient Output Generator" issued on Sep. 7, 1999 having named inventors Weijand et al. Capacitors 1451–1465 are charged by a battery 1467 during a recharging interval (during which a capacitor arrangement forms a charge configuration). If a capacitor pair is charged across battery 1467 in parallel and subsequently discharged across a load in series, the corresponding voltage (as provided to a regulator) is double of the voltage of battery 1467. If a capacitor pair is charged across battery 1467 in series and subsequently discharged across the load in parallel, the corresponding voltage is one half the voltage of battery 1467. The embodiment may utilize capacitor pairs both with a parallel configuration and with a series configuration in order to obtain a desired voltage level to a regulator. Moreover, other embodiments of the invention can utilize other types of capacitor configurations (e.g. capacitor triplets to obtain one third of the battery voltage and capacitor octets to obtain one eighth of the battery voltage) in order to achieve a desired level of voltage granularity to a regulator. Thus, any fraction of the battery voltage can be obtained by a corresponding capacitor configuration In the embodiment, waveform controller 1001 (as instructed by processor 201) configures the capacitor bank through generator control 1003 in order to provide the required voltage inputs (corresponding to 1417–1423) to regulators 1401–1407, respectively (during which the capacitor arrangement forms a stack configuration). Regulators 1401–1407 are instructed to generate stimulation pulses (as illustrated in FIG. 19) at time instances by waveform controller 1001 through control leads 1409–1415, respectively. In the embodiment, a voltage drop across a regulator (e.g. 1401–1407) is determined by a digital to analog converter (DAC) that is associated with the regulator and that is controlled by waveform controller 1001. In the embodiment, waveform controller 1001 can independently control as many as four regulators (1401–1407) in order to form four independent simulation channels, although other embodiments may support a different number of regulators. Each stimulation channel is coupled to electrode controller 1007 through a coupling capacitor (1471–1477). Each stimulation channel can be coupled to at least one of sixteen electrodes (E0–E15). Once again, variations of the embodiment may support different numbers of electrodes. An electrode may be either an anode or a cathode.

Therapy measurement block 221 monitors various components of the stimulation engine system 1400 for performance and diagnostic checks. To assist with its monitoring function, therapy measurement block 221 has associated holding capacitors 1491 and 1493. Once again, variations of the embodiment may support different number of holding capacitors. At least one of the holding capacitors may be redundant in case the first capacitor has failed. As one example, therapy measurement block 221 monitors the voltage across a regulator in order to detect whether there is sufficient "headroom" (which is the voltage difference between the regulator's voltage input and voltage output). Some factors that may alter the "headroom" include a change of the voltage of battery 1467 and changing electrical characteristics of surrounding tissues (for example, caused by a movement in the placement of a lead). If a regulator does not have sufficient headroom, the regulator may not be able to regulate a stimulation pulse that has a constant amplitude over the duration of the pulse. Rather, the amplitude of the stimulation pulse may "droop." In the embodiment, therapy measurement block 221 monitors input 1481 and input 1485 to determine the input voltage and the output voltage of regulator 1401. (In the embodiment, regulators 1403, 1405, and 1407 can be similarly monitored.) Typically the voltage drop across regulator should be 0.3 volts or greater in order to achieve adequate regulation. For example, if therapy measurement block 221 determines that the voltage drop across regulator 1401 is less than a minimum value, then therapy measurement block 221 may notify processor 201 about regulator 1401 experiencing an out-of-regulator condition. In such a case, processor 201 may instruct generator 1003 to associate another capacitor pair to the voltage input of regulator 1401 in order to increase the input voltage. (It is assumed that redundant capacitor pairs are available.) Also, processor 201 may store the occurrence of the out-of-regulator and report the occurrence over a telemetry channel through telemetry module 211. The clinician may wish to recharge battery 1467 in such a case.

If battery 1467 has been recharged after additional capacitor pairs have been configured to compensate for a previous out-of-regulator condition of regulator 1401, the voltage drop across a regulator may be greater than what is necessary to maintain adequate regulation. In such a case, therapy measurement block 221 may remove a capacitor pair that is associated with the voltage input of regulator 1401.

In another embodiment of the invention, therapy measurement block 221 monitors the voltage of battery 1467. If the voltage of battery 1467 is below a threshold value, therapy measurement block 221 reports the low battery condition to processor 201. Consequently, processor 201 may instruct generator 1003 to configure capacitor pairs for the active regulators (e.g. regulators 1401, 1403, 1405, and 1407). (It is assumed that there are a sufficient number of capacitor pairs.). As discussed below, in yet another embodiment of the invention, therapy measurement block 221 monitors various capacitive elements of the stimulation engine system 1400 for possible failure (e.g., holding capacitors 1491 and 1493 and coupling capacitors 1471–1477).

Automatic Waveform Output Adjustment. FIG. 15A shows a logic flow diagram 1500 for detecting an out-of-regulator condition. In step 1501, therapy measurement block 221 measures the voltage drop across a regulator (e.g. regulator 1401). In step 1503, therapy measurement block 221 determines whether the voltage drop is less that a threshold value. If not, therapy measurement block monitors another regulator (e.g. regulator 1403) in step 1505. If so, then therapy measurement block 221 informs INS processor 201 about the out-of-regulator condition in step 1507. In step 1509, it is determined if a capacitor pair is available so that the capacitor pair may be added to the associated capacitor configuration. If so, a capacitor pair is added and another regulator is monitored.

Variations of the embodiment may detect a faulty capacitor of a capacitor pair. For example, if capacitor 1451 (C1) is shorted, the associated voltage across capacitor reduced, causing the voltage drop across the regulator to be reduced. With the logic shown in FIG. 15A, another capacitor pair is configured in order to compensate for capacitor 1451 shorting. Moreover, additional logic steps can be included to detect a faulty capacitor and removing the faulty capacitor from service. In a variation of the embodiment, a capacitor pair is removed from the capacitor arrangement and another capacitor pair is added. If the voltage drop across the regulator is consequently within limits, the capacitor pair that was removed from the configuration is assumed to have a faulty capacitor. If a spare capacitor pair is not available, processor 201 may be notified so that programmer 30 or 35 can be alerted over the telemetry channel. In another embodiment, processor 201 may instruct the INS to shutdown in order to deactivate the generation of a stimulation waveform that is not with an acceptable range.

The embodiment may be used to detect other failure mechanisms. For example, rather than reconfiguring the capacitor configuration, an original regulator can be replaced with a spare regulator. If a voltage drop across the spare regulator is within an acceptable range, then the original regulator is determined to be faulty. However, if it is determined that the original regulator is not faulty, the capacitor arrangement (comprising C1451–1465) can be tested. In one embodiment, the capacitors of the capacitor arrangement can be charged to a known voltage, such as the measured battery voltage, and the voltages across the capacitors can be measured by therapy measurement block 221. If a voltage is low across a capacitor, the capacitor may be determined to be faulty. In such a case the capacitor may be replaced with a redundant capacitor.

Figure 15B:
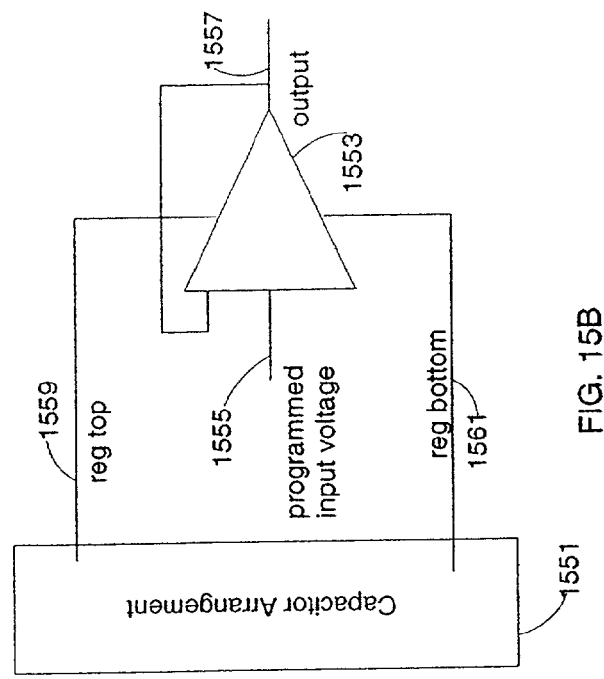
FIG. 15B shows an electrical configuration corresponding to a regulator according to an embodiment of the present invention.
Figure 15A:
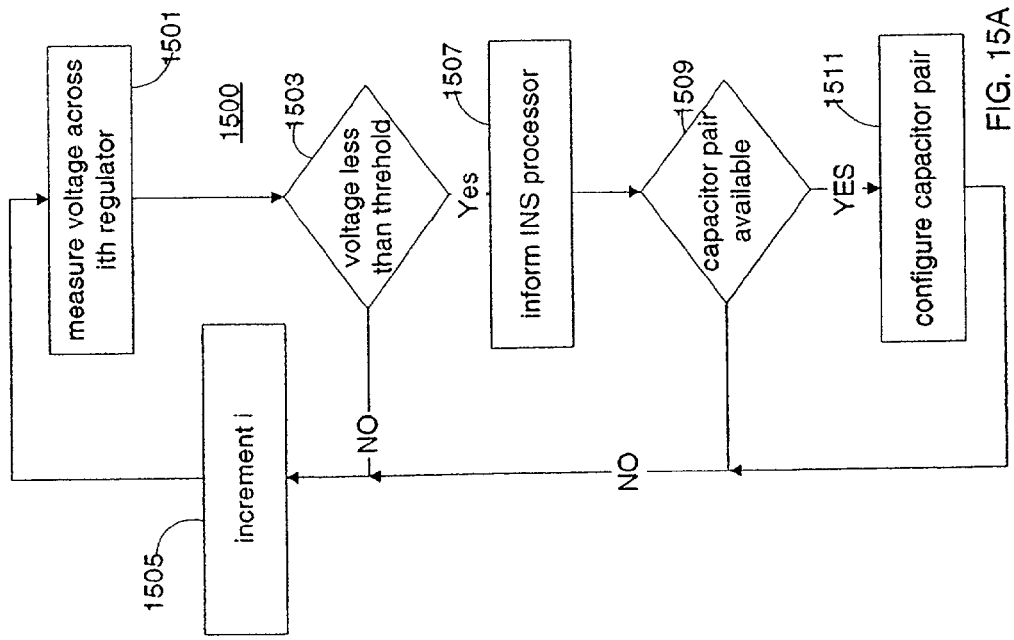
FIG. 15A shows a logic flow diagram for detecting an out-of-regulator condition according to an embodiment of the present invention.

FIG. 15B shows an electrical configuration corresponding to regulators 1401, 1403, 1405, and 1407. The electrical configuration comprises an amplifier 1553 in which an output 1557 feeds into a negative input and a programmed input voltage 1555 feeds into a positive input of amplifier 1553. Thus, amplifier 1553 is configured as a voltage follower amplifier (i.e. output 1557 should approximately equal programmed input voltage 1555 if the circuitry is operating properly). Amplifier 1553 receives a power supply voltage from a capacitor arrangement 1551 through a reg top 1559 and a reg bottom 1561.

The embodiment corresponding to FIG. 15A measures a voltage drop across a regulator (e.g. 1401, 1403, 1405, or 1407). In FIG. 15B, the voltage drop across the regulator corresponds to a voltage difference between reg top 1559 and output 1557. Moreover, other embodiments of the invention may utilize other electrical measurements in order to determine an out-of-regulator condition. In one embodiment, if output 1557 does not approximately equal programmed input voltage 1555, therapy measurement block 221 may determine the occurrence of an out-of-regulator condition. In another embodiment, output 1557 (as measured by therapy measurement block 221) is compared with an expected output voltage. In the embodiment, processor 201 is cognizant of the configuration of capacitor arrangement 1551 and the battery voltage. Processor 201 may use electrical formulae that correspond to the known configuration in order to determine the expected output voltage. A sufficiently large difference between output 1557 and the expected output voltage is indicative of an out-of-regulator condition. In another embodiment, an out-of-regulator condition is detected when the voltage difference between reg top 1559 and reg bottom 1561 (corresponding to an input signal to regulator 1401, 1403, 1405, or 1407) is less than programmed input voltage 1555.

Detection and Correction of Possible Failure of Coupling Capacitor. In the embodiment, a coupling capacitor (e.g. 1471, 1473, 1475, and 1477) is used to transfer charge to an electrode. The accumulated voltage across the coupling capacitor is a measure of the charge that is transferred to the electrode. Moreover, the value of the coupling capacitor determines the maximum charge that can be transferred to the electrode for a given stimulation voltage. However, the coupling capacitor may fail in which the coupling capacitor becomes shorted. In such a case, the coupling capacitor becomes unable to limit excess charge. In order to detect a shorted condition, therapy measurement block 221 monitors the voltage drop across the coupling capacitor (e.g. capacitor 1471 which corresponds to regulator 1401). Inputs 1481 and 1483 enable therapy measurement block 221 to monitor the voltage drop across coupling capacitor 1471. Similar inputs are provided for each other coupling capacitor (1473, 1475, and 1477) in circuit. A voltage drop greater than or less than a prescribed range may be indicative of a possible failure in the coupling capacitor 1471.

Figure 16:
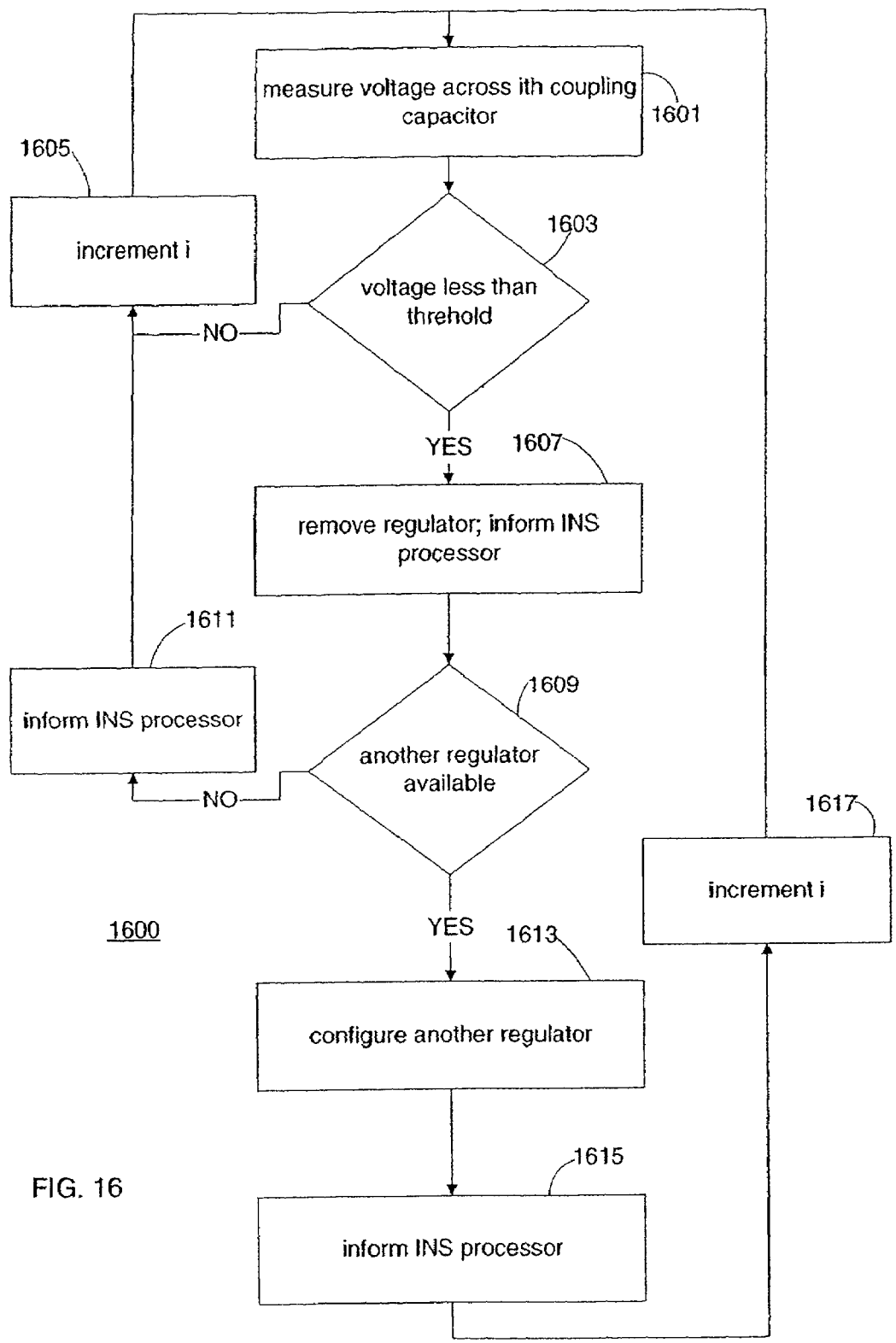
FIG. 16 shows a logic flow diagram for detecting a faulty coupling capacitor according to an embodiment of the present invention.

Once the system detects a failed coupling capacitor, it may take any number of corrective actions including, but not limited to, perform a corrective recharge to compensate for the failure, replacing the failed capacitor with another capacitor, notifying the implantable medical device or the physician programmer, and/or shutting down the implantable medical device. FIG. 16 shows a logic flow diagram 1600 of one embodiment for detecting a faulty coupling capacitor and taking corrective action. In step 1601, therapy measurement block 221 measures the voltage across the coupling capacitor (e.g. coupling capacitor 1471). Although a voltage drop measurement across the coupling capacitor is made, any measurement providing charge information would suffice to determine whether the capacitor has failed including, but not limited to, energy information going in and out of the capacitive element, and current information going in and out of the capacitive element. In step 1603, if it is determined that the voltage drop is less than a predefined threshold, it is assumed that the coupling capacitor has malfunctioned and corrective action should be taken. Otherwise, step 1605 is executed and another coupling capacitor is monitored by therapy measurement block 221.

In step 1607, corrective action is taken by removing from service the coupling capacitor (e.g. coupling capacitor 1471) and its associated regulator (e.g. 1401) and notifying the INS processor 201. In step 1609, logic 1600 determines if a spare capacitor/regulator pair can be configured in order to assume the functionality of the faulty capacitor. In either case, the INS processor 201 may be notified. The INS processor 201 may then notify the clinician (i.e., the physician programmer 30) about the condition through the telemetry channel. If a spare regulator is available, the spare regulator is configured in step 1613 to assume the functionality of the regulator that was removed. INS processor 201 is informed in step 1615. Step 1617 is executed, and another coupling capacitor is monitored. In other embodiments, other forms of corrective action may be taken. For example, the system can provide a charge balance pulse in an amount to compensate for the capacitive element being outside the predefined threshold. The charge balance pulse can be calculated by determining charge going in and going out of the coupling capacitor. For example, if the stimulation pulse is at a constant current, the system can determine the current amount and duration. The charge balance pulse can then be in an amount that zeros out the difference in the charges going in and going out of the coupling capacitor. In another example, the system can just notify the INS processor 201 and physician programmer 30 or it can just simply shut itself down from operation.

Other embodiments of the invention may monitor the coupling capacitor (e.g. coupling capacitor 1471) in order to detect whether the coupling capacitor becomes open. In such a case, the voltage drop across the coupling capacitor may exceed a predefined threshold. In this case, even the associated regulator/capacitor pair may become ineffective in the treatment of the patient. Therapy measurement block 221 may therefore remove the regulator/capacitor pair and configure a spare regulator.

In yet other embodiments, therapy measurement block 221 may measure other elements other than capacitive elements including, but not limited to, holding capacitors 1491 and 1493. In one exemplary embodiment, therapy measurement block 221 measures the voltage of the battery using one of the holding capacitors 1491 or 1493. After a certain time period (e.g., several seconds or several minutes), therapy measurement block 221 re-measures the voltage of the battery using the same holding capacitor 1491 or 1493. Under proper operation of the holding capacitor 1491, the two voltage measurements should be roughly the same. If the two voltage measurements vary by more than a predetermined threshold, however, there is likely a failure in the holding capacitor. Alternatively, if the original voltage measurement of battery is outside a predefined range, it may be indicative of a failed capacitor. For example, if the original voltage measurement of battery is be less than 2V, then it is likely that the holding capacitor has failed. This is the case since if the battery voltage had reached 2V, the circuitry would have already been shut down for purposes of conserving battery resources. In another alternative, if the holding capacitor is open circuited, the therapy measurement block 221 would have been unable to take the initial battery voltage measurement. Once the system determines a possible failure of the holding capacitor, it may then take appropriate action as discussed above (e.g., replacing holding capacitor with redundant capacitor, notifying the implantable medical device or physician programmer of capacitor failure, etc.).

Figure 17:
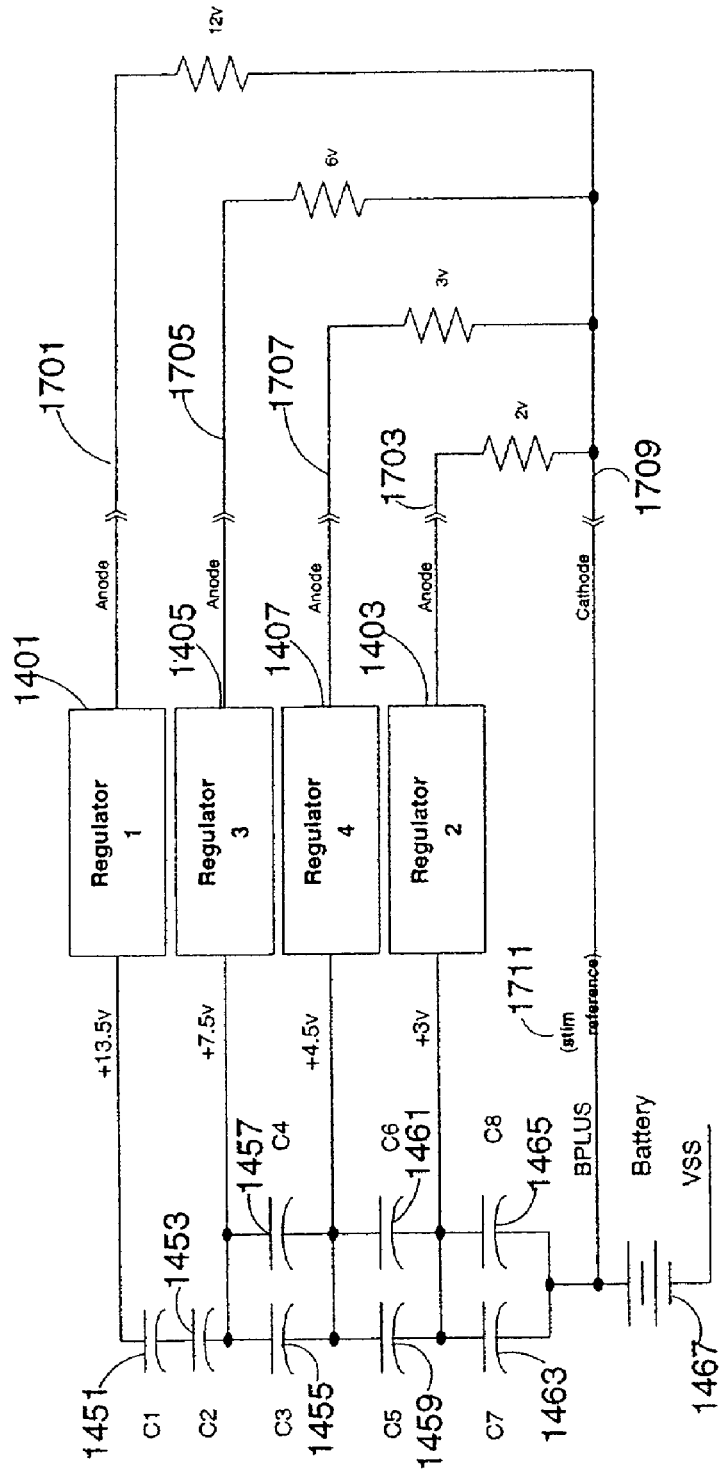
FIG. 17 shows a first configuration for a set of regulators according to an embodiment of the present invention.

Regulator Improvements. FIG. 17 shows a first configuration for a set of regulators comprising regulators 1401, 1403, 1405, and 1407 according to an embodiment of the present invention. The configuration shown in FIG. 17 may be used to generate a Pulse Width "A" pulse (pwa) 1923 that is shown in FIG. 19. Other embodiments may support a different number of regulators in order to generate a different numbers of corresponding waveforms. Capacitors 1451, 1453, 1455, 1457, 1459, 1461, 1463, and 1465 have been charged by battery 1467 so that capacitors 1459 and 1461 have a 1.5 volt potential and capacitors 1451, 1453, 1455, 1457, 1463, and 1465 have a 3.0 volt potential. In order to provide a 3.0 volt input to regulator 1403, a 4.5 volt input to regulator 1407, a 7.5 volt input to regulator 1405, and a 13.5 volt input to regulator 1401, a voltage reference 1711 is configured with respect to BPLUS of battery 1467. Waveform controller 1101 configures the capacitors 1451–1465 and the voltage reference through generator control 1003. The output of regulator 1403 is connected to anode 1703; the output of regulator 1407 is connected to anode 1707; the output of regulator 1405 is connected to anode 1705; the output of regulator 1401 is connected to anode 1701; and voltage reference 1711 is connected to cathode 1709.

Figure 18:
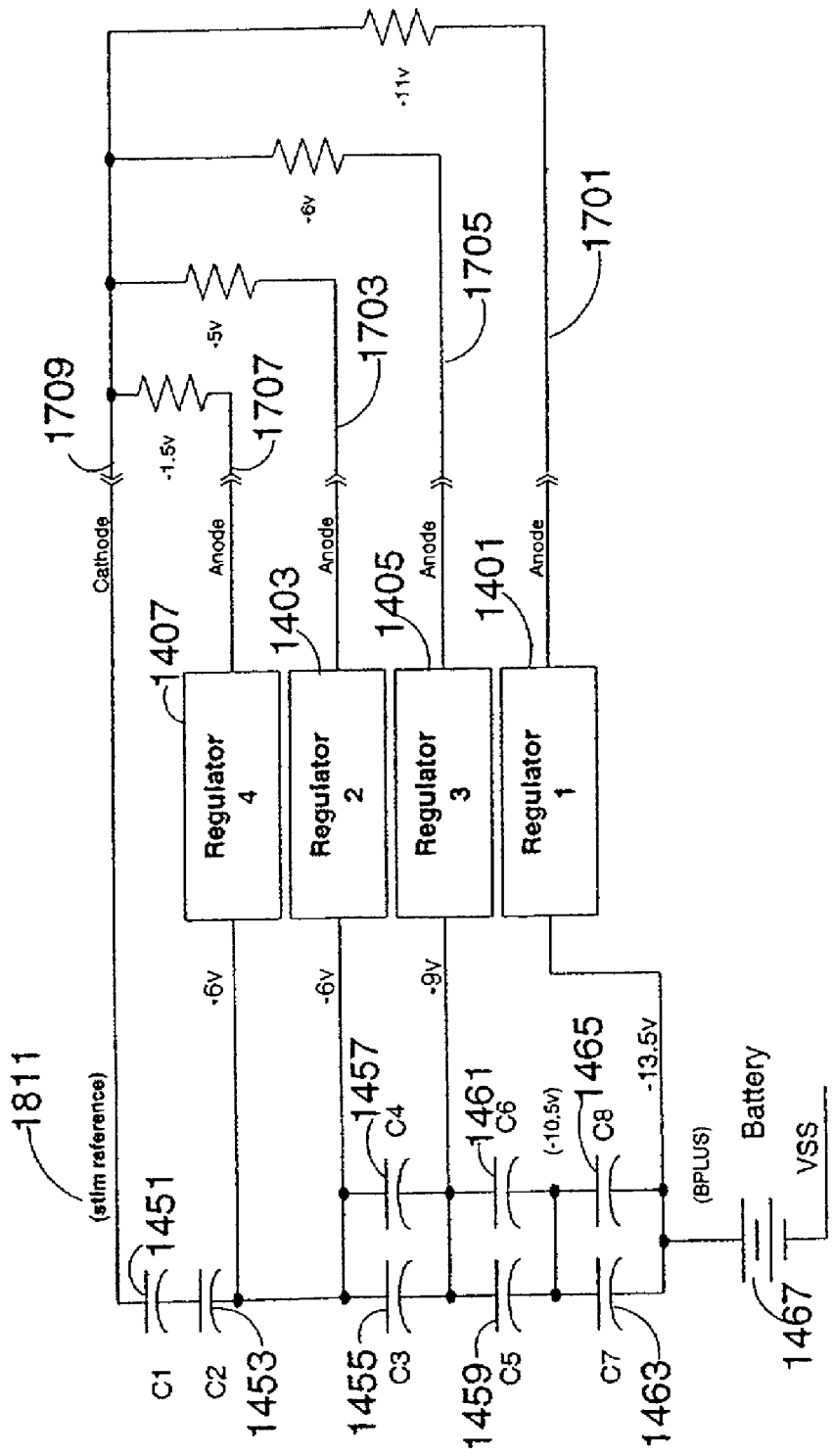
FIG. 18 shows a second configuration for a set of regulators according to an embodiment of the present invention.

FIG. 18 shows a second configuration for a set of regulators comprising regulators 1401, 1403, 1405, and 1407 according to an embodiment of the present invention. The configuration shown in FIG. 18 may be used to generate a pulse width "B" pulse (pwb) 1915 that is shown in FIG. 19. Capacitors 1451–1465 have the same voltage potential as shown in FIG. 17. However, waveform controller 1001 configures a voltage reference 1811 to be the negative side of capacitor 1451 so that the input voltage to each regulator (1407, 1403, 1405, and 1401) has a negative polarity rather than a positive polarity. As in the configuration shown in FIG. 17, cathode 1709 is connected to the voltage reference. Consequently, the voltage outputs of regulators 1407, 1403, 1405, and 1401 have a negative polarity. Waveform controller 1001 also configures capacitors 1451–1465 so that capacitors 1451 and 1453 are between voltage reference 1811 and the input of regulators 1407 and 1403, capacitors 1451, 1453, 1455, 1457 are between voltage reference 1811 and the input of regulator 1405, and capacitors 1451, 1453, 1455, 1457, 1459, 1461, 1463, and 1465 are between voltage reference 1811 and the input of regulator 1401.

Table 1 compares the voltage outputs of regulators 1401, 1403, 1405, and 1407 in FIGS. 17 and 18.

TABLE 1

Comparison of Regulator Output Voltages for pwa and pwb Configurations

| | Pulse Width A Configuration | Pulse Width B Configuration |
|---|---|---|
| Anode 1701 | 12 volts | −11 volts |
| Anode 1703 | 2 volts | −5 volts |
| Anode 1705 | 6 volts | −6 volts |
| Anode 1707 | 3 volts | −1.5 volts |

With regulators 1401, 1403, 1405, and 1407 having a capability of generating negative voltage, the risk of a charge accumulation that may damage surrounding tissue around stimulated electrodes is reduced. The required amplitude of a stimulation pulse pwa 1923 (as shown in FIG. 19) varies with the type of therapy.

With a therapy pulse (e.g. pwa 1923) that is delivered to the tissue, it may be necessary to retract an equal amount of charge from the same tissue after the therapy pulse is completed. This retraction of charge is typically done in the form of a secondary pulse, or recharge pulse, which causes an equal amount of charge to flow in the opposite direction of the original therapy pulse. If the amount of charge in the secondary pulse does not equal the amount of charge in the therapy pulse, charge will accumulate on the electrode surface, and the chemical reactions at the electrode-tissue interface will not remain balanced, which can cause tissue and electrode damage. For example, the accumulated charge may be accompanied by electrolysis, thus causing hydrogen, oxygen and hydroxyl ions to form. As a result, the pH level of the immediate layer of fluid in the proximity of the electrode may deviate from its norm. PH variations may oscillate between pH 4 and pH 10 within a few microns of the electrode. Also, charge accumulation may cause dissolution of the electrode (e.g. platinum), resulting in lead corrosion and possible damage to tissue that encounters the resulting chemical migration. Thus, the reduction of the net charge that accumulates in the region of the treatment reduces the possibility of accompanying tissue damage and electrode damage.

As will be discussed in the context of FIG. 19, pwb pulse 1925 may have a negative polarity (as supported by the regulator configuration in FIG. 18). The negative charge that accumulates in the surrounding tissue during pwb pulse 1925 counterpoises the positive charge that accumulates during pwa pulse 1923.

If the electrical characteristics between a stimulated electrode pair can be modeled as an equivalent circuit having a capacitor, the charge accumulated during pwa interval 1909 may be counterpoised by the charge accumulated during pwb interval 1915 if the product (amplitude of pwa 1923) * (interval of pwa 1909) approximately equals the product (amplitude of pwb 1925) * (interval of pwb 1915) when the polarities of pwa pulse 1923 and pwb pulse 1925 are opposite of each other.

Other embodiments of the invention may generate positive and negative current waveforms by converting a voltage pulse to a current pulse, in which the output from the regulator is driven through a resistance in the regulator.

Recharge Delay and Second Pulse Generation. FIG. 19 shows stimulation waveform 1901 according to an embodiment of the present invention. FIG. 19 shows waveform 1901 spanning a rate period interval 1902. Waveform 1901 may repeat or may change waveform characteristics (corresponding to changing a waveform parameter) during a next rate period interval. Stimulation waveform 1901 may be programmed in order to customize a therapeutical treatment to the needs of the patient. An initial delay (delay_1) interval 1905 commences with a rate trigger event. The rate trigger event occurs at the beginning of each rate period interval. During a pulse width A (pwa) setup interval 1907, capacitors 1451–1465 are moved from a charge configuration to a stack configuration. A pulse width pwa interval 1909 commences upon the completion of interval 1907. During interval 1909, regulators 1401–1407 apply voltage or current outputs to a set of electrodes (e.g. anodes) while corresponding electrodes (e.g. cathodes) are connected to a stimulation voltage reference. In the embodiment, pwa interval 1909 is programmable from 0 to 655 msec with increments of 10 microseconds, in which an associated timer is a 16-bit timer.

A second delay (delay_2) interval 1911 may begin upon the completion of pwa interval 1909. During interval 1911, all electrode connections remain open. In the embodiment, second delay interval 1911 is programmable from 0 to 655 msec with increments of 10 microseconds.

A pwb setup interval 1913 may begin upon the completion of second delay interval 1911. During interval 1913, capacitors 1451–1465 are moved from a charge configuration to a stack configuration. A pwb interval 1915 follows interval 1913. During pwb interval 1915, regulators 1401–1407 apply voltage or current outputs to the set of electrodes (e.g. anodes) while corresponding electrodes (e.g. cathodes) are connected to a stimulation voltage reference. In the embodiment, pwb interval 1915 is programmable from 0 to 655 with increments of 10 microseconds.

Wile the embodiment configures the stimulation pulse during pwa interval 1909 with a positive polarity and the stimulation pulse during pwb interval 1915 with a negative polarity, other embodiments may reverse the polarities. Moreover, other embodiments may configure both pulses during intervals 1909 and 1915 to have the same polarity.

A third delay (delay_3) interval 1917 begins upon completion of pwb interval 1915. During interval 1917, all electrodes connections remain open. In the embodiment, the third delay interval 1917 is programmable from 0 to 655 msec with increments of 10 microseconds.

A passive recharge interval 1919 is triggered by the completion third delay interval 1917. During interval 1919, electrodes may be connected to a system ground. In the embodiment, waveform controller 1001 (through passive recharge control 1491) passively recharges the connected electrodes in order to provide a charge balance in tissues that are adjacent to the connected electrodes. Passive recharging during interval 1919 may function to complete the recharging process that may be associated with pwb interval 1915. In the embodiment, passive recharge interval 1919 is programmable from 0 to 655 msec with increments of 10 microseconds. A wait interval 1921 follows interval 1919 in order to complete rate period interval 1902. In the embodiment, the rate period interval is programmable from 0 to 655 msec. In the embodiment, if the sum of the component intervals (1905, 1907, 1909, 1911, 1913, 1915, 1917, 1919, and 1921) exceed the rate period interval, the rate period interval takes precedence over all components intervals in the event of a conflict. For example, all waveform timers are reloaded and a new waveform may commence with the occurrence of rate trigger event.

Pulses generated during pwa pulse interval 1909 and pwb interval 1915 may be used to stimulate surrounding tissues or may be used to assist in charge balancing. The effects of charge balancing during a pulse may be combined with charge balancing during passive recharge interval 1919 in order to obtain a desired charge balancing. (Recharging may provide charge balancing with active components or with passive components or both.)

Other embodiments of the invention may initiate rate period interval 1902 with a different interval than delay_1 interval 1905. For example, other embodiments may define the beginning of rate period interval 1902 with passive recharge interval 1919. Moreover, with the embodiment or with other embodiments, any of the delay intervals (delay_1 interval 1905, delay_2 interval 1911, delay_3 interval 1917, wait interval 1921), pulse intervals (pwa interval 1909, pwb interval 1915), setup intervals (pwa setup interval 1907, pwb setup interval 1913), or passive recharge interval 1919 may be effectively deleted by setting the corresponding value to approximately zero. Also, other embodiments may utilize different time increments other than 10 microseconds.

FIG. 19 also shows a second waveform 1903 that is formed during the formation of 1901. (In the embodiment, regulators 1401 and 1407 may be utilized to form four waveforms.) Waveform 1903 is phased with waveform 1901 (with each waveform having the same rate period interval). A pwa pulse 1927 (that is associated with waveform 1903) occurs after the completion of pwa pulse 1923 (that is associated with waveform 1901). The clinician may stimulate a set of electrodes with waveform 1901. The subsequent stimulation of the set of electrodes by waveform 1903 may cause the firing of the neurons that may not be possible only with waveform 1901 or 1903 alone. In the embodiment, waveforms 1901 (corresponding to regulator 1401) and 1903 (corresponding to regulator 1403) may be applied to the same electrode or to two electrodes in close proximity. In the embodiment, if regulators 1401 and 1405 are configured to the same electrode, regulators 1401 and 1405 are configured in series for voltage amplitude waveforms and in parallel for current amplitude waveforms.

In the embodiment, the rate period interval of waveforms 1901 and 1903 are the same. However, other embodiments of the invention may utilize different rates periods for different waveforms.

Figure 20:
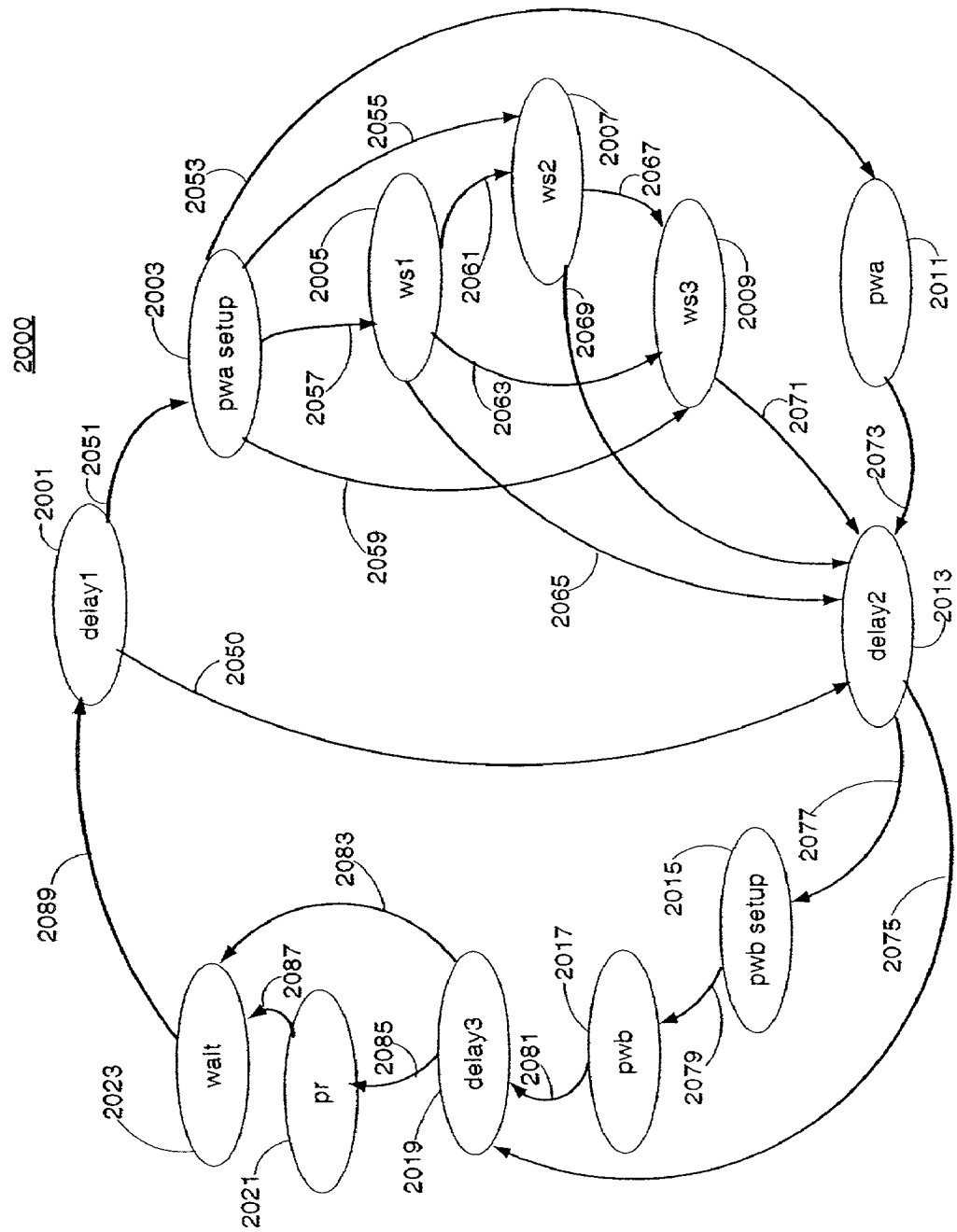
FIG. 20 shows a state diagram for a finite state machine to form the stimulation waveform as shown in FIG. 19 according to an embodiment of the present invention.

FIG. 20 shows a state diagram that a finite state machine 2000 utilizes to form the waveforms as shown in FIG. 19 according to an embodiment of the present invention. A finite state machine may be associated with each waveform that is generated by INS 200. In the embodiment, state machine 2000 is implemented with waveform controller 1001. Waveform controller 1001, in accordance with state machine 2000, controls generator 1003, regulators 1401–1407, passive recharge control 1491, and electrode control 1007 in order to generate stimulation pulses in accordance with state machine 2000. Moreover, waveform controller 1001 may obtain waveform parameters from processor 201. The clinician may alter a waveform parameter (e.g. pwa pulse duration 1909) by sending an instruction over the telemetry channel through telemetry unit 211 to processor 201 in order to modify the waveform parameter. In the discussion of FIG. 19, it is assumed that wave shaping (as will be discussed in the context of FIG. 21) is not activated. In FIG. 20, a state delay_1 2001 corresponds to first delay interval 1905. A transition 2051 initiates a state pwa setup 2003 upon the expiration of interval 1905. State 2003 corresponds to pwa setup interval 1913. If wave shaping is activated, states ws_1 2005, ws_2 2007, and ws_3 2009 may be executed. (However, discussion of states 2005, 2007, and 2009 are deferred until the discussion of FIG. 21.) A delay_2 state 2013 may be accessed directly from state delay_1 2001 through transition 2050 if pwa pulse is not generated during pwa interval 1909.

Assuming that wave shaping is not activated, a state pwa 2011 is executed upon the completion of pwa setup interval 1907 through a transition 2053. State pwa 2011 corresponds to interval pwa 1909 during which pwa pulse 1923 is generated. Upon the completion of interval 1909, state delay_2 2013 is entered through a transition 2073. State 2013 corresponds to delay_2 interval 1911. If pwb pulse is generated, a pwb setup state 2015 is entered through transition 2077 upon the completion of delay_2 interval 1911. If pwb pulse 1925 is not generated, a delay_3 state 2019 is entered through transition 2075 upon the completion of delay_2 interval 1911. State pwb setup 2015 corresponds to pwb setup interval 1913 and state delay_3 state 2019 corresponds to delay_3 interval 1917.

With the completion of pwb setup interval 1913, if pwb pulse 1925 is to be generated, a pwb state 2017 is entered through transition 2079. The pwb state 2017 corresponds to pwb interval 1915 during which the pwb pulse 1925 is generated. Upon the completion of pwb interval 1915, delay_3 state 2019 is entered through transition 2081. Upon the completion of delay_3 interval 1917, finite state machine enters a passive recharge (pr) state 2021 through transition 2085 or a wait state 2023 through transition 2083. The pr state 2021 may be circumvented if recharging during pwb 2017 state adequately eliminates a charge accumulation that occurs during pwa state 2003. The pr state 2001 corresponds to passive charge interval 1919. Upon the completion of passive recharge interval 1919, state machine 2000 enters wait state 2023, and remains in state 2023 until the completion of the rate period interval. State machine 2000 consequently repeats the execution of states 2001–2023.

Other embodiments of the invention may support a different number of stimulation pulses (e.g. three, four, and so forth) during rate period interval 1902.

Figure 21:
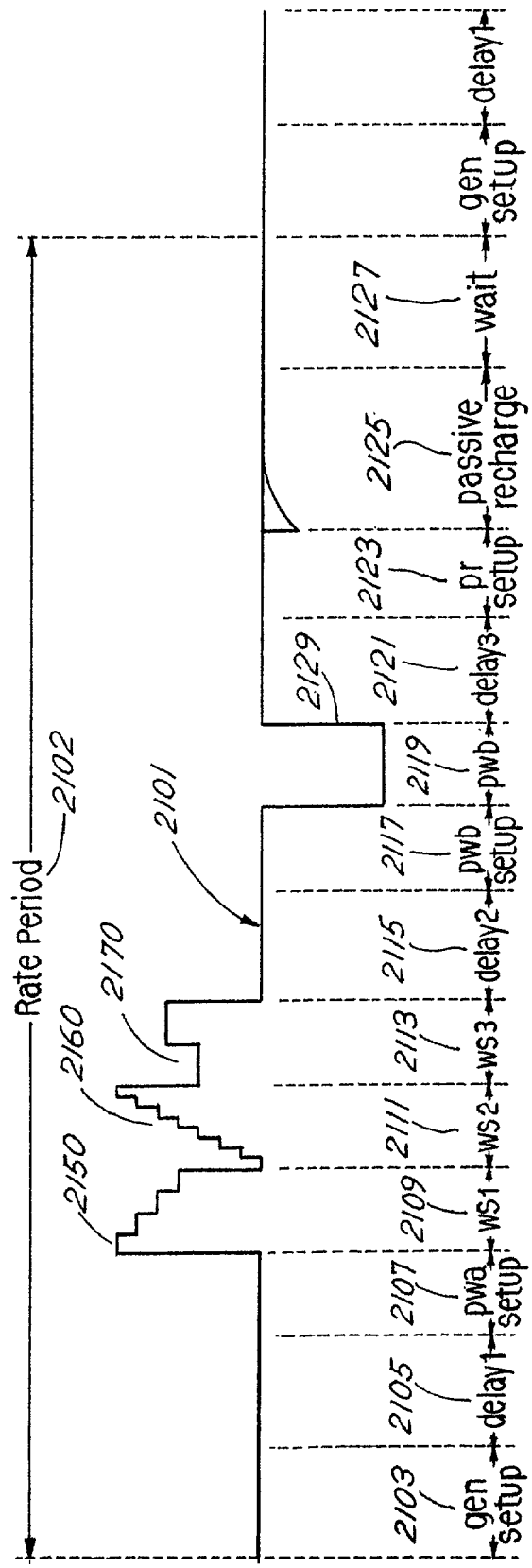
FIG. 21 shows wave shaping of a stimulation pulse shown in FIG. 19 according to an embodiment of the present invention.

Wave Shaping. FIG. 21 shows a waveform 2101 in which stimulation pulse pwa 1923 is generated by wave shaping according to an embodiment of the present invention. Waveform 2101, as shown in FIG. 21, spans a rate period interval 2102. Wave shaping of pwa 1923 corresponds to a state ws_1 2005, a state ws_2 2007, and a state ws_3 2009 (as shown in finite state machine 2000 in FIG. 20) and corresponds to a ws_1 duration 2109, a ws_2 duration 2111, and a ws_3 duration 2113 in FIG. 21. Durations 2109, 2111, and 2113 correspond to phases 1, 2, and 3 of pwa pulse 1923. In the embodiment, pwa pulse 1923 is synthesized in order to adjust the therapeutical effectiveness of pwa pulse 1923. In the embodiment, without wave shaping, pwa pulse 1923 is essentially a rectangular pulse (flat-topped) as illustrated in FIG. 19.

In the embodiment, pwa interval 1909 is subdivided into three phase intervals 2109, 2111, and 2113. During phase intervals 2109, 2111, or 2113, at least one parameter is associated with the stimulation waveform. In the embodiment, a parameter may correspond to characteristics of the stimulation waveform (e.g. a desired amount of rise during the phase) or may correspond to an electrode configuration in which the stimulation waveform is applied. In the embodiment, all other time intervals remain the same and all time intervals maintain the same order of succession (e.g. pwb 1925 follows pwa 1923) as in the case without wave shaping. During each of the three phases (ws_1 2150, ws_2 2160, and ws_3 2170) of pwa pulse 1923, the output amplitude may be rising, falling, or constant across a phase. (Other embodiments may utilize a different number of phases. Typically, with a greater number of phases, one can achieve a better approximation of a desired waveform. The desired waveform may correspond to any mathematical function, including a ramp, a sinusoidal wave, and so forth.) Each of the three phases is defined by a register containing an initial output amplitude, a register containing a final output amplitude, and a register containing a number of clock periods in which the amplitude output remains constant across an incremental step. In the embodiment, a phase duration (e.g. 2109, 2111, and 2113) is determined by:

$$(|\text{final amplitude count} - \text{initial amplitude}|+1)*(\text{number of clock periods per step})$$

The output amplitude changes by one amplitude step after remaining at the previous amplitude for a clock count equal to the value of the clock periods per step as contained in a register. The output amplitude range setting in a register determines a size of an amplitude step. (In the embodiment, the step size may equal 10, 50, or 200 millivolts.)

An example of wave shaping illustrates the embodiment as shown in FIG. 21. The step size is 500 millivolts for phases 2150 and 2160 and 1 volt for phase 2170. The master waveform generator clock is 10 microseconds. Durations 2109, 2111, and 2113 are each 400 microseconds. During duration 2109, the initial amplitude register contains 70 ($46_{16}$) and the final amplitude register contains 40 ($28_{16}$). The clock periods per step is 10 or 100 microseconds (10 * 10 microseconds). During duration 2109, waveform 2103 starts at 3.5 volts and descends 0.5 volts every 100 microseconds until the amplitude value is 2.0 volts.

During duration 2111, the initial amplitude register contains 0 and the final amplitude register contains 70 ($46_{16}$). The clock periods per step is 10. During duration 2111, waveform 2105 starts at 0 volts and ascends 0.5 volts every 100 microseconds until the amplitude value is 3.5 volts. During duration 2113, the initial amplitude register contains 30 ($1E_{16}$). The clock periods per step is 20 (corresponding to 200 microseconds). During duration 2113, waveform 2107 starts at 1.5 volts and ascends to 2.5 volts in one step.

Finite state machine 2000 (as shown in FIG. 20) supports wave shaping with ws_1 state 2005, ws_2 state 2007, and ws_3 state 2009. With wave shaping enabled, state 2005, 2007, or 2009 is entered from pwa setup state 2003 through transitions 2057, 2055, and 2059, respectively. The pwa state is not executed when wave shaping is enabled. In the embodiment, the synthesis associated with any phase (2150, 2160, 2170) may be circumvented. For example, ws_1 state 2005 may enter ws_2 state 2007 through transition 2061, may enter ws_3 state 2009 through transition 2063, or may enter delay_2 state 2013 through transition 2065.

Other embodiments of the invention may support a different number of phases than is utilized in the exemplary embodiment. Also, other embodiments may utilize wave shaping for other portions of waveform 2101 (e.g. a pwb pulse 2129).

Figure 22:
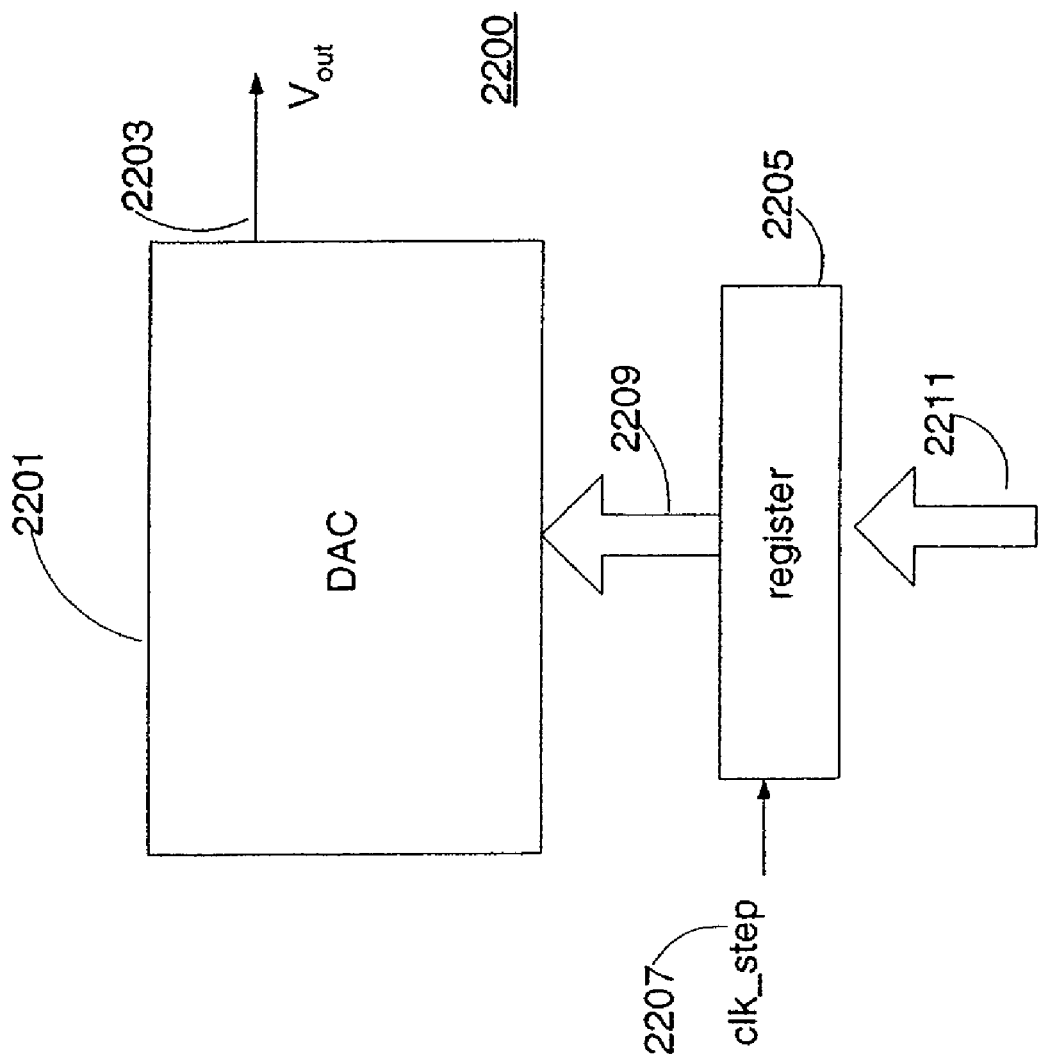
FIG. 22 shows a first apparatus that supports wave shaping as shown in FIG. 21 according to an embodiment of the present invention.

FIG. 22 shows a first apparatus that supports wave shaping as shown in FIG. 19 according to an embodiment of the present invention. Output voltage $V_{out}$ 2203 corresponds to phase 2150, 2160, or 2170. A digital to analog converter (DAC) 2201 generates $V_{out}$ 2203 in accordance to a digital input 2209. Input 2209 is obtained from register 2205. Register 2205 receives a digital input 2211 from waveform controller 1001. Input 2211 is stored in register 2205 when clocked by clk_step 2207, which occurs at a rate of updating phases 2150, 2160, or 2170 (corresponding to a "step"). Waveform controller 1001 updates digital input 2211 in order to cause $V_{out}$ 2203 to equal a desired value during phases 2150, 2160, or 2170 in accordance with an initial output amplitude, a final output amplitude, an amplitude step size, and a step time duration parameters.

In a variation of the embodiment, DAC 2201 determines a voltage drop across a regulator (e.g. 1401, 1403, 1405, or 1407). The value of the stimulation waveform (with a voltage amplitude) is approximately a voltage input to the regulator minus the voltage drop (as determined by DAC 2201). Consequently, digital input 2211 is determined by subtracting an approximate value of the stimulation waveform from the input voltage to the regulator.

Figure 23:
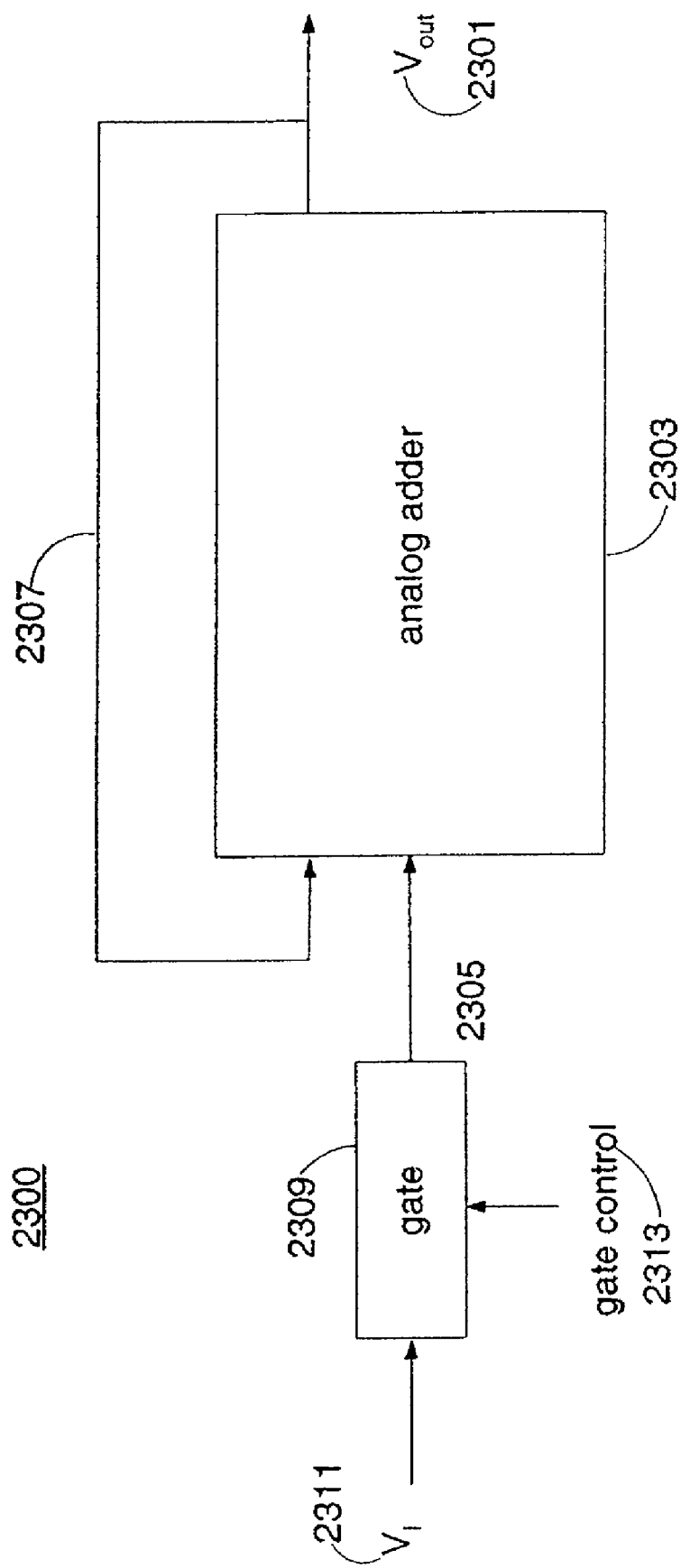
FIG. 23 shows a second apparatus that supports wave shaping as shown in FIG. 21 according to an embodiment of the present invention.

FIG. 23 shows a second apparatus that supports wave shaping as shown in FIG. 19 according to an embodiment of the present invention. An output $V_{out}$ 2301 corresponds to phases 2150, 2160, and 2170 in FIG. 21. $V_{out}$ 2301 is the output of an analog adder 2303 having inputs 2305 and 2307. Input 2305 is obtained from a gate 2309 in which a step voltage $V_i$ 2311 is gated by a gate control 2313 in accordance with a step time duration. With apparatus 2300, $$Vout = Vout + Vin$$

Figure 24:
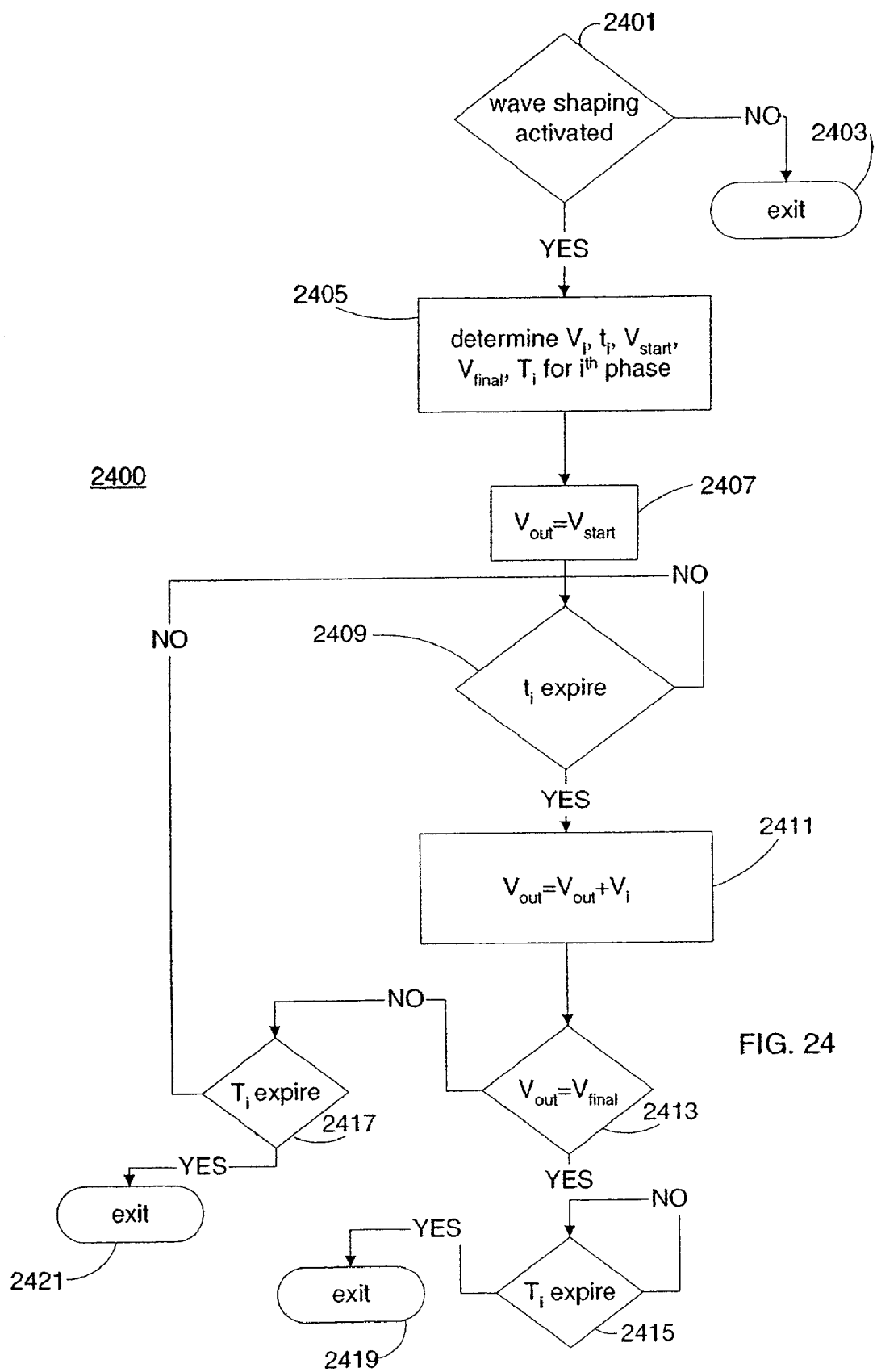
FIG. 24 shows a logic flow diagram representing a method for supporting wave shaping according to an embodiment of the present invention.

FIG. 24 shows a logic flow diagram 2400 representing a method for supporting wave shaping according to an embodiment of the present invention. Step 2401 determines whether wave shaping is activated. If not, process 2400 is exited in step 2403. In such a case, pwa stimulation pulse 1923 is generated as an essentially flat pulse over time duration 1909. If wave shaping for an $i^{th}$ phase of the pwa pulse is activated, step 2405 is executed.

In step 2405, an initial output voltage $V_{start}$, a final output voltage $V_{final}$, a step size $V_i$, a step duration $t_i$, and a phase time duration $T_i$ are determined. In step 2407, $V_{out}$ is equal to $V_{start}$. Step 2409 determines if the step time duration $t_i$ has expired. If so, $V_{out}$ is incremented by the step size $V_i$ in step 2411. If $V_{out}$ equals the final output voltage $V_{final}$ in step 2413, the output voltage $V_{out}$ remains constant until the end of the phase duration $T_i$ in step 2415. If $V_{out}$ is not equal to the final output voltage $V_{final}$ and the phase time duration $T_i$ has not expired (as determined in step 2417), step 2409 is repeated in order to update $V_{out}$ for another step time duration $t_i$.

Other embodiments of the invention may support wave shaping of a current amplitude of waveform 2101. In such cases, a voltage amplitude may be converted into a current amplitude by driving a resistor that is associated with a regulator (e.g. 1401, 1403, 1405, and 1407).

Figure 25:
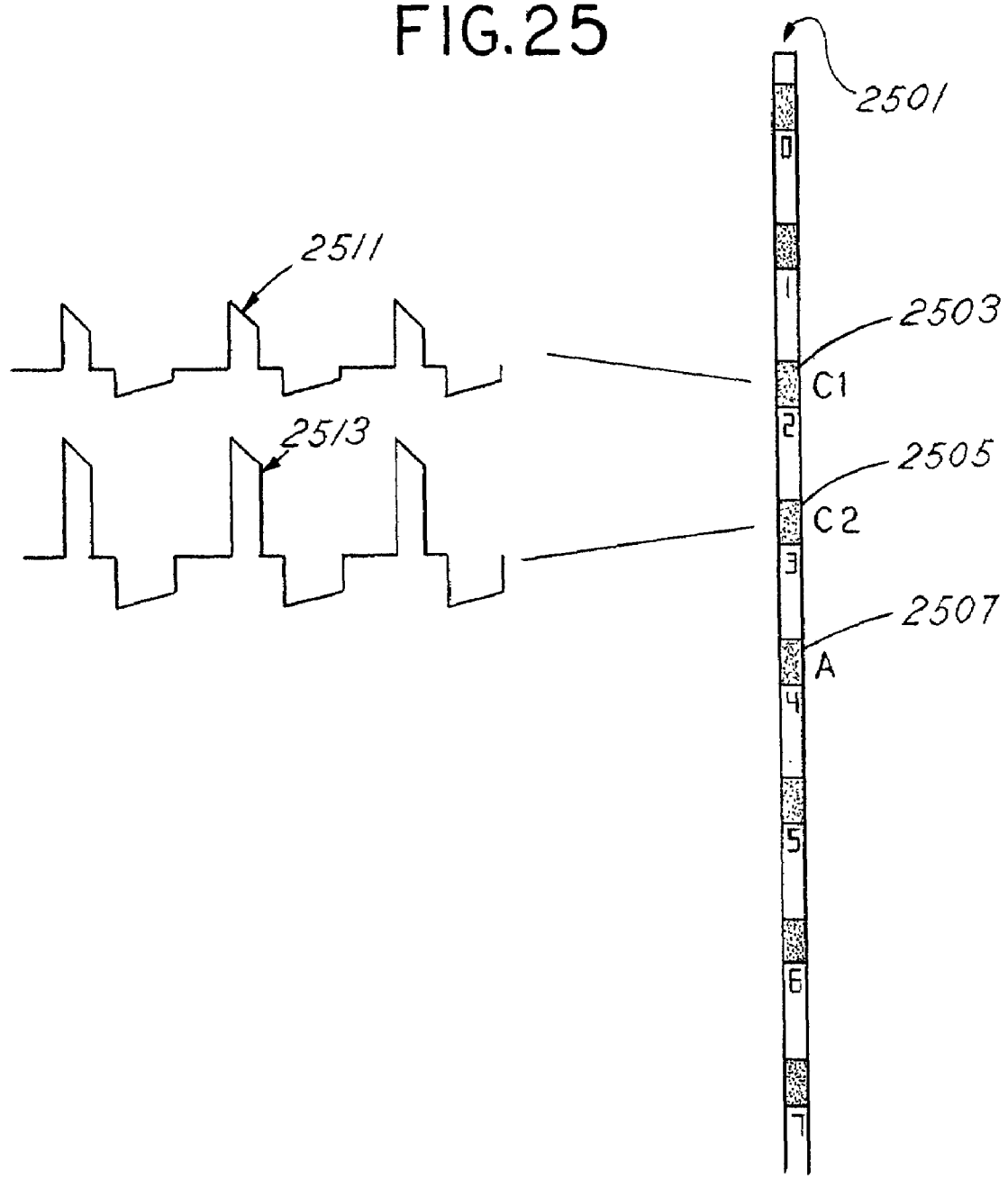
FIG. 25 shows a stimulation arrangement according to prior art.

Simultaneous Delivery of a Plurality of Independent Therapy Programs. FIG. 25 shows a stimulation arrangement that is associated with an implantable neuro stimulator according with prior art such as that disclosed in U.S. Pat. No. 5,895,416. Lead 2501 comprises a plurality of electrodes including cathode 2503, cathode 2505, and anode 2507. Anode 2507 provides a common reference for either a voltage amplitude pulse or a current amplitude pulse through cathodes 2503 and 2505. Waveforms 2511 and 2513 are applied to cathodes 2503 and 2505, respectively. Waveform 2511 differs from waveform 2513 by amplitude scaling; however, component time durations are the same for waveform 2511 and waveform 2513. Moreover, the waveforms serve to treat the same neurological condition in a specific portion of the body.

Figure 26:
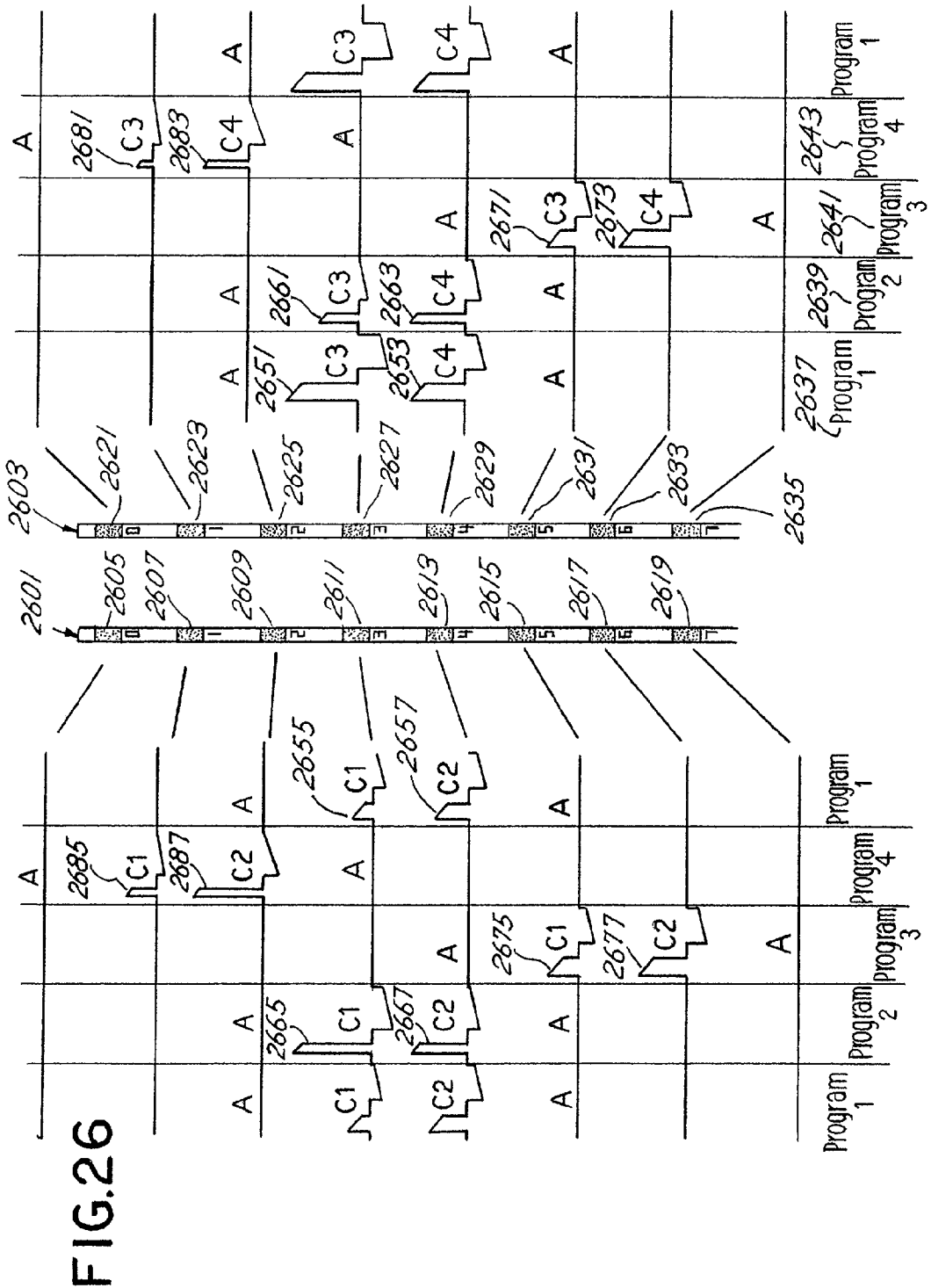
FIG. 26 shows a stimulation arrangement according to an embodiment of the present invention.

FIG. 26 shows a stimulation electrode arrangement that is associated with INS 200 according to an embodiment of the present invention. INS 200 stimulates leads 2601 and 2603. Lead 2601 comprises electrodes 2605-2619, and lead 2603 comprises electrodes 2621-2635. The basic "unit" of therapy is a "therapy program" in which amplitude characteristics, pulse width, and electrode configuration are associated with a pulse train for treatment of a specific neurological conduction in a specific portion of the body. Multiple therapy programs may therefore be used to either treat distinct neurological conditions or treat the same neurological condition but in distinct areas of the body. The pulse train may comprise a plurality of pulses (voltage or current amplitude) that are delivered essentially simultaneously to the electrode configuration.

In FIG. 26, four therapy programs (program 2637, program 2639, program 2641, and program 2643) are configured and activated. In the embodiment, thirty two therapy programs may be defined in which one to four therapy programs may be activated to form a therapy program set. (Other embodiments may support a different number of therapy programs and a different size of the therapy program set.)

Additional therapy programs (not directly accessible by the patient) may be provided for any number of reasons including, for example and without limitation, to treat neurological conditions in distinct parts of the body, to treat distinct neurological conditions, to support sub-threshold measurements, patient notification, and measurement functions. For example, a patient notification program is used to define an output pulse train for patient notification such as some type of patterned stimulation that can be discernable by the patient. The patient notification program may be activated by a low battery (battery 1467) condition. A lead integrity measurement program defines a pulse train to executing lead (e.g. 2601 and 2603) integrity measurements.

In FIG. 26, the therapy program set comprises therapy programs 2637 (program 1), 2639 (program 2), 2641 (program 3), and 2643 (program 4). Each therapy program comprises four waveforms C1, C2, C3, and C4 that are generated by regulators 1401, 1403, 1405, and 1407, respectively. Table 2 illustrates the configuration of the program set as shown in FIG. 26. Stimulation pulses are applied to cathodes 2607–2617 of lead 2601 and to cathodes 2623–2633 of lead 2603, while anodes 2605, 2619, 2621, and 2635 serve as common references.

TABLE 2

EXAMPLE OF THERAPY PROGRAM SET

| Electrode | Lead 1 (2601) | | | | | | Lead 2 (2603) | | | | | |
|---|---|---|---|---|---|---|---|---|---|---|---|---|
|  | 1 | 2 | 3 | 4 | 5 | 6 | 1 | 2 | 3 | 4 | 5 | 6 |
| program 1 (2637) |  |  | C1 | C2 |  |  |  |  | C3 | C4 |  |  |
| program 2 (2639) |  |  | C1 | C2 |  |  |  |  | C3 | C4 |  |  |
| program 3 (2641) |  |  |  |  | C1 | C2 |  |  |  |  | C3 | C4 |
| program 4 (2643) | C1 | C2 |  |  |  |  | C3 | C4 |  |  |  |  |

With therapy program 2637 (program 1), stimulation pulses 2655, 2657, 2651, and 2653 are applied to cathodes 2611, 2613, 2627, and 2629, respectively. With therapy program 2639 (program 2), stimulation pulses 2665, 2667, 2661, and 2663 are applied to cathodes 2611, 2613, 2627, and 2629, respectively. The pulse characteristics of a regulator (e.g. 1401, 1403, 1405, 1407) may vary from one therapy program to another. For example, pulse 2655 and pulse 2665 are generated by regulator 1401; however, pulse 2655 and pulse 2665 may have different characteristics in order to obtain a desired therapeutical effect.

With therapy program 2641 (program 3), stimulation pulses 2675, 2677, 2671, and 2673 are applied to cathodes 2615, 2617, 2631, and 2633, respectively. With therapy program 2643 (program 4), stimulation pulses 2685, 2687, 2681, and 2683 are applied to cathodes 2607, 2609, 2623, and 2625, respectively.

One skilled in the art will appreciate that the present invention can be practiced with embodiments other than those disclosed. The disclosed embodiments are presented for purposes of illustration and not limitation, and the present invention is limited only by the claims that follow.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Thus, embodiments of the AUTOMATIC WAVEFORM OUTPUT ADJUSTMENT FOR AN IMPLANTABLE MEDICAL DEVICE are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An apparatus for automatic waveform output adjustment with an implantable medical device, comprising in combination:
    a first regulator module operatively connected to an electrode, the first regulator configured to direct a first pulse with a first amplitude to the electrode, the regulator further configured to adjust the amplitude of the first pulse;
    a measurement module that performs an electrical measurement that is associated with the first regulator module;
    a generator connected to the first regulator module in order to provide an input signal to the first regulator module; and
    a processor connected to the measurement module the generator, the processor configured to perform:
        (a) receiving the electrical measurement, the electrical measurement indicative of the amplitude of the pulse;
        (b) determining a differential value between the electrical measurement and a desired value adapted to be stored in memory;
        (c) ascertaining whether the generator shall be reconfigured in order for the generator to deliver the input signal that corresponds to approximately the desired value; and
        (d) instructing the generator in response to (c).

2. The apparatus of claim 1, wherein the electrical measurement corresponds to a voltage drop across the first regulator module.

3. The apparatus of claim 1, including a programmed input voltage, wherein the electrical measurement corresponds to a voltage potential between an output of the first regulator module and the programmed input voltage.

4. The apparatus of claim 1, wherein the electrical measurement corresponds to a difference between a measured output and an expected output value of the first regulator module.

5. The apparatus of claim 1, wherein the electrical measurement corresponds to a voltage of the input signal that is provided to the first regulator module by the generator, and wherein the processor is configured to further perform:
    (e) comparing the voltage of the input signal to a programed input voltage.

6. The apparatus of claim 1, wherein the electrical measurement corresponds to an output of the first regulator module, and wherein the processor is configured to further perform:
    (e) determining the desired value from a configuration of the generator, the generator comprising a capacitor arrangement.

7. The apparatus of claim 1, wherein (d) comprises:
    (i) reconfiguring the generator in order that the generator delivers the input signal corresponding to approximately the desired value.

8. The apparatus of claim 1, wherein the amplitude corresponds to a value of voltage.

9. The apparatus of claim 1, wherein the amplitude corresponds to a value of current.

10. The apparatus of claim 1, wherein the generator comprises capacitor arrangement, the capacitor arrangement comprising a plurality of capacitor pairs.

11. The apparatus of claim 10, wherein step (c) comprises the steps of:
   (i) determining if there is a faulty capacitor pair; and
   (ii) determining if there is a spare capacitor pair.

12. The apparatus of claim 11, wherein (d) comprises:
   (i) instructing the generator to activate the spare capacitor pair if the faulty capacitor pair is detected.

13. The apparatus of claim 11, wherein (d) comprises:
   (i) instructing the generator to deactivate the faulty capacitor pair if the faulty capacitor pair is detected.

14. The apparatus of claim 11, wherein (i) comprises:
   (1) charging a capacitor of the capacitor arrangement to a known voltage;
   (2) measuring a measured voltage across the capacitor; and
   (3) comparing the measured voltage with the known voltage.

15. The apparatus of claim 14, wherein (i) further comprises:
   (4) repeating (1)–(3) for each capacitor of the capacitor arrangement.

16. The apparatus of claim 1, wherein the apparatus further comprises a second regulator module, the second regulator connected to the electrode and configured to direct a second pulse having a second amplitude to the electrode wherein the electrical measurement provided by the measurement module is a first electrical measurement and the measurement module performs a second electrical measurement that is associated with the second regulator module, and wherein the processor is configured to perform the further steps of:
   (e) comparing corresponding measurements of the first regulator nodule and the second regulator module; and
   (f) replacing the first regulator module with the second regulator module in response to (e).

17. The apparatus of claim 1, wherein the processor is further configured to perform:
   (e) notifying a programming unit in response to (c).

18. The apparatus of claim 17, wherein the implantable medical device includes a telemetry module and (e) utilizes the telemetry module.

19. The apparatus of claim 1, wherein the regulator module comprises a voltage regulator.

20. The apparatus of claim 1, wherein the regulator module comprises a current regulator.

21. A method for automatic waveform output adjustment with an implantable medical device, the method comprising:
   (a) receiving an electrical measurement, the electrical measurement indicative of an amplitude of a pulse;
   (b) determining a differential value between the electrical measurement and a desired value;
   (c) ascertaining whether a generator shall be reconfigured in order for the generator to deliver an input signal that corresponds to approximately the desired value, the ascertaining including:
      (i) determining if there is a faulty capacitor pair; and
      (ii) determining if there is a spare capacitor pair; and
   (d) instructing the generator in response to step (c).

22. The method of claim 21, wherein (d) comprises:
   (i) instructing the generator to activate the spare capacitor pair if the faulty capacitor pair is detected.

23. The method of claim 21, wherein (d) comprises:
   (i) instructing the generator to deactivate the faulty capacitor pair if the faulty capacitor pair is detected.

24. The method of claim 21, wherein (i) comprises:
   (1) charging a capacitor of a capacitor arrangement to a known voltage;
   (2) measuring a measured voltage across the capacitor; and
   (3) comparing the measured voltage with the known voltage.

25. The method of claim 24, (i) further comprising:
   (4) repeating (1)–(3) for each capacitor of the capacitor arrangement.

* * * * *